United States Patent
Golz et al.

(10) Patent No.: US 7,338,781 B2
(45) Date of Patent: Mar. 4, 2008

(54) ORGANIC ANION TRANSPORTING (OAT)-LIKE PROTEIN UST3-LIKE1 AND USES THEREOF

(75) Inventors: Stefan Golz, Essen (DE); Ulf Brüggemeier, Leichlingen (DE); Andreas Geerts, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/548,420

(22) PCT Filed: Mar. 4, 2004

(86) PCT No.: PCT/EP2004/002172

§ 371 (c)(1),
(2), (4) Date: Jun. 5, 2006

(87) PCT Pub. No.: WO2004/081041

PCT Pub. Date: Sep. 23, 2004

(65) Prior Publication Data

US 2007/0031938 A1    Feb. 8, 2007

(30) Foreign Application Priority Data

Mar. 10, 2003  (EP) .................... 03004939

(51) Int. Cl.
*C21P 21/06*  (2006.01)
*C07K 14/00*  (2006.01)

(52) U.S. Cl. .................. 435/69.1; 435/320.1; 435/325; 435/252.3; 536/23.1; 530/350

(58) Field of Classification Search ............... 536/23.1; 435/320.1, 252.3, 325, 69.1; 530/350
See application file for complete search history.

(56) References Cited

FOREIGN PATENT DOCUMENTS

WO    WO 02/04520 A    1/2002
WO    WO 02/079252 A   10/2002

OTHER PUBLICATIONS

Sekine et al.: "The multispecific organic anion transporter (OAT) family"; Pfluegers Archiv, Springer Verlag, vol. 440, No. 3, Jul. 2000, pp. 337-350, XP002214979.

Belinsky et l.: "Characterization of Moat-C and Moat-D New Members of the MRP/Cmoat Subfamily of Transporter Proteins", Journal of the National Cancer Institute, vol. 90, No. 22, Nov. 18, 1998, pp. 1735-1741, XP002921303.

*Primary Examiner*—Karen Cochrane Carlson
(74) *Attorney, Agent, or Firm*—Banner & Witcoff, Ltd.

(57) ABSTRACT

The present invention is directed to a polynucleotide sequence of a novel organic anion transporting (OAT)-like protein UST3-like1. More particularly, the present invention provides a polynucleotide sequence comprising the nucleic acid sequence SEQ ID NO: 1 or nucleic acid sequences that hybridize to SEQ ID NO: 1 or its complimentary strand. The invention also provides the human UST3-LIKE1 associated with the gastrointestinal and liver diseases, metabolic diseases, hematological disorders, respiratory diseases, neurological disorders, urological disorders and cardiovascular diseases as a result of relative quantification of the mRNA distribution in different human tissues by expression profiling. The invention also provides assays for the identification of compounds useful for the modulation of said diseases. The methods of the invention involve cell-free and cell-based assays that identify compounds which bind to and/or activate or inhibit the activity of UST3-LIKE1, a organic anion transporting (OAT)-like protein, followed by an in vivo assay of the effect of the compound on said diseases. The invention also features compounds which bind to and/or activate or inhibit the activity of UST3-LIKE1 as well as pharmaceutical compositions comprising such compounds.

12 Claims, 2 Drawing Sheets

Fig. 1

SEQ ID NO:1

```
tttgaacttatctggatacagtcattttgtctcctcttggggatcact
tgtccagcctcaatggcctttcaggacctcctagatcaagttggaggc
ctggggagattccagatccttcagatggttttccttataatgttcaac
gtcatagtataccatcaaactcagctggagaacttcgcagcattcata
cttgatcatcgctgctggttcatatactggacaatgacactatccct
gacaatgaccctgggaccctcagccaggatgcctcctgagaatctcc
atcccattcgactcaaatctgaggccagagaagtgtcgtcgctttgtc
catcccagtggaagctcattcatctgaatgggaccttccccaacacg
agtgagccagatacagagccctgtgtggatggctgggtatatgaccaa
agctccttcccttccaccattgtgactaagggttttccttttcttccgg
tgggatctggtatgcgaatctcaaccactgaattcagtagctaaattt
ctattcatggctggaatgatggtgggaggcaacctatatggccatttg
tcagacaggtttgggagaaagttcgtgctcagatggtcttacctccag
ctcgccattgtaggcacctgtgcggcctttgctcccaccatcctcgta
tactgctcctgcgcttcttggctggggctgctacatttagcatcatt
gtaaatactgttttgttaattgtagagtggataactcaccaattctgt
gccatggcattgacattgacactttgtgctgctagtattggacatata
accctgggaagcctggcttttgtcattcgagaccagtgcatcctccag
ttggtgatgtctgcaccatgctttgtcttctttctgttctcaaggtgg
ctggcagagtctgctcggtggctcattatcaacaacaaaccagaagag
ggcttaaaggaacttagaaaagctgcacacaggaatggaatgaagaat
gctgaagacatcctaaccatggaggttttgaaatccaccatgaagcaa
gaactggaggcagcacagaaaagcattctctttgtgaattgctccgc
atcccaacatatgtaaaagaatctgtttcctgtcctttgtgagattt
gcaagtaccatccttttggggccttactttgcacctccagcatctg
ggaaacaatgttttcctgttgcagactctctttggtgcagtcaccctc
ctggccaattgtgttgcaccttgggcactgaatcacatgagccgtcga
ctaagccagatgcttctcatgttcctactggcaacctgccttctggcc
atcatatttgtgcctcaagaaatgcagaccctgcgtgtggttttggca
accctgggtgtgggagctgcttctcttggcattacctgttctactgcc
caagaaaatgaactaattccttccataatcaggggaagagctactgga
atcactggaaactttgctaatattggggagccctggcttccctcatg
atgatcctaagcatatattctcgaccctgccctggatcatctatgga
gtctttgccatcctctctggccttgttgtcctcctccttcctgaaacc
aggaaccagcctcttcttgacagcatccaggatgtggaaatgagatg
ctccagaaaagcagggcaggaagatacctgcagcaaagtgacacaatt
ttaaggaattccaggtgctgattgctgattaaacagcaagataaagga
aaaatcgagaccatttctagatactactaaaatttagaaataaataa
ataacaagatataatggataaatacattccatttacaactgtgattct
aaatggttaaatataaaatatctacaaataatcataagaa
```

Fig. 2:
SEQ ID NO:2
MAFQDLLDQVGGLGRFQILQMVFLIMFNVIVYHQTQLENFAAFILDHR
CWVHILDNDTIPDNDPGTLSQDALLRISIPFDSNLRPEKCRRFVHPQW
KLIHLNGTFPNTSEPDTEPCVDGWVYDQSSFPSTIVTKGFLFFRWDLV
CESQPLNSVAKFLFMAGMMVGGNLYGHLSDRFGRKFVLRWSYLQLAIV
GTCAAFAPTILVYCSLRFLAGAATFSIIVNTVLLIVEWITHQFCAMAL
TLTLCAASIGHITLGSLAFVIRDQCILQLVMSAPCFVFFLFSRWLAES
ARWLIINNKPEEGLKELRKAAHRNGMKNAEDILTMEVLKSTMKQELEA
AQKKHSLCELLRIPNICKRICFLSFVRFASTIPFWGLTLHLQHLGNNV
FLLQTLFGAVTLLANCVAPWALNHMSRRLSQMLLMFLLATCLLAIIFV
PQEMQTLRVVLATLGVGAASLGITCSTAQENELIPSIIRGRATGITGN
FANIGGALASLMMILSIYSRPLPWIIYGVFAILSGLVVLLLPETRNQP
LLDSIQDVENEMLQKSRAGRYLQQSDTILRNSRC

Fig. 3:
SEQ ID NO:3
5`-TATACTGCTCCCTGCGCTTC-3

Fig. 4:
SEQ ID NO:4
5`-TGGCTGGGGCTGCTACATTTAGCAT-3

Fig. 5:
SEQ ID NO:5
5`- CACAGAATTGGTGAGTTATCCACT-3`

SEQUENCE LISTING

```
<160> NUMBER OF SEQ ID NOS: 5

<210> SEQ ID NO 1
<211> LENGTH: 1912
<212> TYPE: DNA
<213> ORGANISM: Homo sapiens

<400> SEQUENCE: 1
tttgaactta tctggataca gtcatttgt ctcctcttgg ggatcacttg tccagcctca        60
atggcctttc aggacctcct agatcaagtt ggaggcctgg ggagattcca gatccttcag      120
atggttttcc ttataatgtt caacgtcata gtataccatc aaactcagct ggagaacttc      180
gcagcattca tacttgatca tcgctgctgg gttcatatac tggacaatga cactatccct      240
gacaatgacc ctgggaccct cagccaggat gccctcctga gaatctccat cccattcgac      300
tcaaatctga ggccagagaa gtgtcgtcgc tttgtccatc cccagtggaa gctcattcat      360
```

-continued

```
ctgaatggga ccttccccaa cacgagtgag ccagatacag agccctgtgt ggatggctgg    420
gtatatgacc aaagctcctt cccttccacc attgtgacta agggtttcct tttcttccgg    480
tgggatctgg tatgcgaatc tcaaccactg aattcagtag ctaaatttct attcatggct    540
ggaatgatgg tgggaggcaa cctatatggc catttgtcag acaggtttgg gagaaagttc    600
gtgctcagat ggtcttacct ccagctcgcc attgtaggca cctgtgcggc ctttgctccc    660
accatcctcg tatactgctc cctgcgcttc ttggctgggg ctgctacatt tagcatcatt    720
gtaaatactg ttttgttaat tgtagagtgg ataactcacc aattctgtgc catggcattg    780
acattgacac tttgtgctgc tagtattgga catataaccc tgggaagcct ggcttttgtc    840
attcgagacc agtgcatcct ccagttggtg atgtctgcac catgctttgt cttctttctg    900
ttctcaaggt ggctggcaga gtctgctcgg tggctcatta tcaacaacaa accagaagag    960
ggcttaaagg aacttagaaa agctgcacac aggaatggaa tgaagaatgc tgaagacatc   1020
ctaaccatgg aggttttgaa atccaccatg aagcaagaac tggaggcagc acagaaaaag   1080
cattctcttt gtgaattgct ccgcataccc aacatatgta aaagaatctg ttcctgtcc    1140 tttgtgagat ttgcaagtac catccctttt tggggcctta ctttgcacct ccagcatctg   1200
ggaaacaatg ttttcctgtt gcagactctc tttggtgcag tcaccctcct ggccaattgt   1260
gttgcacctt gggcactgaa tcacatgagc cgtcgactaa gccagatgct tctcatgttc   1320
ctactggcaa cctgccttct ggccatcata tttgtgcctc aagaaatgca gaccctgcgt   1380
gtggttttgg caaccctggg tgtgggagct gcttctcttg gcattacctg ttctactgcc   1440
caagaaaatg aactaattcc ttccataatc aggggaagag ctactggaat cactggaaac   1500
tttgctaata ttgggggagc cctggcttcc ctcatgatga tcctaagcat atattctcga   1560
cccctgccct ggatcatcta tggagtcttt gccatcctct ctggccttgt tgtcctcctc   1620
cttcctgaaa ccaggaacca gcctcttctt gacagcatcc aggatgtgga aaatgagatg   1680
ctccagaaaa gcagggcagg aagatacctg cagcaaagtg acacaatttt aaggaattcc   1740
aggtgctgat tgctgattaa acagcaagat aaaggaaaaa tcgagaccat ttctagatac   1800
tactaaaatt tagaaaataa ataaataaca agatataatg gataaataca ttccatttac   1860
aactgtgatt ctaatggtt aaatataaaa tatctacaaa taatcataag aa             1912
```

<210> SEQ ID NO 2
<211> LENGTH: 562
<212> TYPE: PRT
<213> ORGANISM: Homo sapiens

<400> SEQUENCE: 2

```
Met Ala Phe Gln Asp Leu Leu Asp Gln Val Gly Gly Leu Gly Arg Phe
1               5                   10                  15

Gln Ile Leu Gln Met Val Phe Leu Ile Met Phe Asn Val Ile Val Tyr
            20                  25                  30

His Gln Thr Gln Leu Glu Asn Phe Ala Ala Phe Ile Leu Asp His Arg
        35                  40                  45

Cys Trp Val His Ile Leu Asp Asn Asp Thr Ile Pro Asp Asn Asp Pro
    50                  55                  60

Gly Thr Leu Ser Gln Asp Ala Leu Leu Arg Ile Ser Ile Pro Phe Asp
65                  70                  75                  80

Ser Asn Leu Arg Pro Glu Lys Cys Arg Arg Phe Val His Pro Gln Trp
                85                  90                  95
```

```
Lys Leu Ile His Leu Asn Gly Thr Phe Pro Asn Thr Ser Glu Pro Asp
                100                 105                 110

Thr Glu Pro Cys Val Asp Gly Val Tyr Asp Gln Ser Ser Phe Pro
            115                 120                 125

Ser Thr Ile Val Thr Lys Gly Phe Leu Phe Arg Trp Asp Leu Val
130                 135                 140

Cys Glu Ser Gln Pro Leu Asn Ser Val Ala Lys Phe Leu Phe Met Ala
145                 150                 155                 160

Gly Met Met Val Gly Gly Asn Leu Tyr Gly His Leu Ser Asp Arg Phe
                165                 170                 175

Gly Arg Lys Phe Val Leu Arg Trp Ser Tyr Leu Gln Leu Ala Ile Val
                180                 185                 190

Gly Thr Cys Ala Ala Phe Ala Pro Thr Ile Leu Val Tyr Cys Ser Leu
                195                 200                 205

Arg Phe Leu Ala Gly Ala Ala Thr Phe Ser Ile Ile Val Asn Thr Val
            210                 215                 220

Leu Leu Ile Val Glu Trp Ile Thr His Gln Phe Cys Ala Met Ala Leu
225                 230                 235                 240

Thr Leu Thr Leu Cys Ala Ala Ser Ile Gly His Ile Thr Leu Gly Ser
                245                 250                 255

Leu Ala Phe Val Ile Arg Asp Gln Cys Ile Leu Gln Leu Val Met Ser
                260                 265                 270

Ala Pro Cys Phe Val Phe Phe Leu Phe Ser Arg Trp Leu Ala Glu Ser
            275                 280                 285

Ala Arg Trp Leu Ile Ile Asn Asn Lys Pro Glu Glu Gly Leu Lys Glu
            290                 295                 300

Leu Arg Lys Ala Ala His Arg Asn Gly Met Lys Asn Ala Glu Asp Ile
305                 310                 315                 320

Leu Thr Met Glu Val Leu Lys Ser Thr Met Lys Gln Glu Leu Glu Ala
                325                 330                 335

Ala Gln Lys Lys His Ser Leu Cys Glu Leu Leu Arg Ile Pro Asn Ile
                340                 345                 350

Cys Lys Arg Ile Cys Phe Leu Ser Phe Val Arg Phe Ala Ser Thr Ile
            355                 360                 365

Pro Phe Trp Gly Leu Thr Leu His Leu Gln His Leu Gly Asn Asn Val
            370                 375                 380

Phe Leu Leu Gln Thr Leu Phe Gly Ala Val Thr Leu Leu Ala Asn Cys
385                 390                 395                 400

Val Ala Pro Trp Ala Leu Asn His Met Ser Arg Arg Leu Ser Gln Met
                405                 410                 415

Leu Leu Met Phe Leu Leu Ala Thr Cys Leu Leu Ala Ile Ile Phe Val
                420                 425                 430

Pro Gln Glu Met Gln Thr Leu Arg Val Val Leu Ala Thr Leu Gly Val
            435                 440                 445

Gly Ala Ala Ser Leu Gly Ile Thr Cys Ser Thr Ala Gln Glu Asn Glu
            450                 455                 460

Leu Ile Pro Ser Ile Ile Arg Gly Arg Ala Thr Gly Ile Thr Gly Asn
465                 470                 475                 480

Phe Ala Asn Ile Gly Gly Ala Leu Ala Ser Leu Met Met Ile Leu Ser
                485                 490                 495

Ile Tyr Ser Arg Pro Leu Pro Trp Ile Ile Tyr Gly Val Phe Ala Ile
            500                 505                 510

Leu Ser Gly Leu Val Val Leu Leu Leu Pro Glu Thr Arg Asn Gln Pro
```

-continued

```
                515                 520                 525
Leu Leu Asp Ser Ile Gln Asp Val Glu Asn Glu Met Leu Gln Lys Ser
        530                 535                 540

Arg Ala Gly Arg Tyr Leu Gln Gln Ser Asp Thr Ile Leu Arg Asn Ser
545                 550                 555                 560

Arg Cys

<210> SEQ ID NO 3
<211> LENGTH: 20
<212> TYPE: DNA
<213> ORGANISM: artificial sequence
<220> FEATURE:
<223> OTHER INFORMATION: forward primer

<400> SEQUENCE: 3
tatactgctc cctgcgcttc                                              20

<210> SEQ ID NO 4
<211> LENGTH: 25
<212> TYPE: DNA
<213> ORGANISM: artificial sequence
<220> FEATURE:
<223> OTHER INFORMATION: reverse primer

<400> SEQUENCE: 4
tggctggggc tgctacattt agcat                                        25

<210> SEQ ID NO 5
<211> LENGTH: 24
<212> TYPE: DNA
<213> ORGANISM: artificial sequence
<220> FEATURE:
<223> OTHER INFORMATION: probe

<400> SEQUENCE: 5
cacagaattg gtgagttatc cact                                         24
```

ORGANIC ANION TRANSPORTING (OAT)-LIKE PROTEIN UST3-LIKE1 AND USES THEREOF

CROSS-REFERENCE TO RELATED APPLICATIONS

This application is a national state application of PCT/EP04/02172, filed Mar. 4, 2004, which claims foreign priority to European patent application 03004939.9, filed Mar. 10, 2003. These applications are incorporated herein by reference in their entireties.

TECHNICAL FIELD OF THE INVENTION

The present invention is in the field of molecular biology; more particularly, the present invention describes a nucleic acid sequence and an amino acid sequence for a novel human UST3-LIKE1 and its regulation for therapeutic purposes.

BACKGROUND OF THE INVENTION

Organic anion transporting (OAT) polypeptides play an important role in the uptake of organic anions, including bile acids, bilirubin conjugates and sulfobromophthalein, in the liver (Hsiang et al., J. Biol. Chem. 274, 37161-68, 1999; Konig et al., Am. J. Physiol. Gastrointest. Liver Physiol. 278, G156-64, 2000; Kouzuki et al., J. Pharmacol. Exp. Ther. 292, 505-11, 2000). Thus, levels of organic anion transporting polypeptides can be modulated to affect the rate of drug clearance via hepatocellular uptake. Further, OATs have been found to transport eicosanoids, taurocholate, conjugated steroids, and thyroid hormones.

SUMMARY OF THE INVENTION

The invention relates to a nucleotide sequence which encodes a novel human UST3-LIKE1. In the following UST3-LIKE1 designates a polypeptide having the sequence of or being homologous to SEQ ID NO:2, and having UST3-LIKE1 activity. UST3-LIKE1 further contemplates various polypeptides arising from post-translational modifications of the polypeptide including but not limited to acetylation, carboxylation, glycosylation, phosphorylation, lipidation and acylation. The invention relates to nucleic acid molecules encoding UST3-LIKE1 and polypeptides having UST3-LIKE1-activity, and to their use in the diagnosis or treatment of diseases associated with expression of UST3-LIKE1.

It is an object of the invention to provide reagents and methods for regulating the expression and activity of human UST3-LIKE1 for the treatment of gastrointestinal and liver diseases, metabolic diseases, hematological disorders, respiratory diseases, neurological disorders, urological disorders and cardiovascular diseases. This and other objects of the invention are provided by one or more of the embodiments described below.

Another object of the invention is a method of screening for agents which can regulate the activity of UST3-LIKE1. A test compound is contacted with a polypeptide comprising the amino acid sequence selected of the group consisting of SEQ ID NO:2 or a polypeptide which exhibits UST3-LIKE1 activity and is encoded by a polynucleotide hybridizing under stringent conditions to polynucleotide shown in SEQ ID NO:1; and binding of the test compound to UST3-LIKE1 is detected, wherein a test compound which binds to the polypeptide is identified as a potential therapeutic agent for decreasing the activity of UST3-LIKE1. Another embodiment of the invention is a method of screening for agents which can regulate the activity of UST3-LIKE1. A test compound contacted with a polypeptide comprising the amino acid sequence selected from a group consisting of SEQ ID NO:2 or a polypeptide which exhibits UST3-LIKE1 activity and is encoded by a polynucleotide hybridizing under stringent conditions to polynucleotide shown in SEQ ID NO:1; and UST3-LIKE1 activity of the polypeptide is detected, wherein a test compound which increases UST3-LIKE1 activity is identified as a potential therapeutic agent for increasing the activity of UST3-LIKE1, and wherein a test compound which decreases UST3-LIKE1 activity of the polypeptide is identified as a potential therapeutic agent for decreasing the activity of UST3-LIKE1.

Another object of the invention is a method of screening for agents which can regulate the activity of UST3-LIKE1. A test compound is contacted with a polynucleotide comprising the sequence selected of the group consisting of (1) SEQ ID NO:1 or (2) a polynucleotide which encodes a polypeptide exhibiting UST3-LIKE1 activity and hybridizes under stringent conditions to the polynucleotide shown in SEQ ID NO:1; and binding of the test compound to the polynucleotide is detected, wherein a test compound which binds to the polynucleotide is identified as a potential therapeutic agent for decreasing the activity of UST3-LIKE1.

Another object of the invention is a method of screening for agents which can regulate the activity of UST3-LIKE1. A test compound is contacted with a product encoded by a polynucleotide which comprises the nucleotide sequence shown in SEQ ID NO:1; and binding of the test compound to the product is detected, wherein a test compound which binds to the product is identified as a potential agent for regulating the activity of UST3-LIKE1.

Another object of the invention is a method of reducing the activity of UST3-LIKE1. A cell is contacted with a reagent which specifically binds to a polynucleotide encoding UST3-LIKE1 or the UST3-LIKE1 polypeptide. UST3-LIKE1 activity is thereby reduced.

Another object of the invention is a method of increasing the activity of UST3-LIKE1. A cell is contacted with a reagent which specifically binds to a polynucleotide encoding UST3-LIKE1 or the UST3-LIKE1 polypeptide. UST3-LIKE1 activity is thereby increased.

Another object of the invention is the antisense DNA of DNA encoding UST3-LIKE1; cloning or expression vectors containing nucleic acid encoding UST3-LIKE1; host cells or organisms transformed with expression vectors containing nucleic acid encoding-UST3-LIKE1; a method for the production and recovery of purified UST3-LIKE1 from host cells: purified protein, UST3-LIKE1, which can be used to identify inhibitors or activators of signal transduction involving UST3-LIKE1; and methods of screening for ligands of UST3-LIKE1 using transformed cells.

BRIEF DESCRIPTION OF THE DRAWINGS

FIG. 1 shows the nucleotide sequence of a UST3-LIKE1 polynucleotide (SEQ ID NO:1).

FIG. 2 shows the amino acid sequence of a UST3-LIKE1 polypolypeptide (SEQ ID NO:2).

FIG. 3 shows the nucleotide sequence of a primer useful for the invention (SEQ ID NO:3).

FIG. 4 shows the nucleotide sequence of a primer useful for the invention (SEQ ID NO:4).

FIG. 5 shows the nucleotide sequence of a primer useful for the invention (SEQ ID NO:5).

DETAILED DESCRIPTION OF THE INVENTION

Nucleotide Sequence

As used herein and designated by the upper case abbreviation, UST3-LIKE1, refers to an transporter in either naturally occurring or synthetic form and active fragments thereof which have the amino acid sequence of SEQ ID NO:2. In one embodiment, the polypeptide UST3-LIKE1 is encoded by mRNAs transcribed from the cDNA, as designated by the lower case abbreviation, UST3-LIKE1, of SEQ. ID NO: 1.

The novel human UST3-LIKE1 shows a homology of 83% to the human SCL22A9 transporter (Genbank: NM_080866.1). The sequence of UST3-LIKE1 was assembled from genomic sequences (AP003420).

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal, or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or may be chemically synthesized. They are useful in detecting the presence of identical or similar sequences. Such probes may be labeled with reporter molecules using nick translation, Klenow fill-in reaction, PCR or other methods well known in the art. Nucleic acid probes may be used in southern, northern or in situ hybridizations to determine whether DNA or RNA encoding a certain protein is present in a cell type, tissue, or organ.

A fragment of a polynucleotide or nucleic acid that comprises all or any part of the nucleotide sequence having fewer nucleotides than about 6 kb, preferably fewer than about 1 kb which can be used as a probe.

"Reporter" molecules are radionuclides, enzymes, fluorescent, chemiluminescent, or chromogenic agents which associate with a particular nucleotide or amino acid sequence, thereby establishing the presence of a certain sequence, or allowing for the quantification of a certain sequence.

"Recombinant nucleotide variants" encoding UST3-LIKE1 may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one or several of the following UST3-LIKE1 characteristics: cellular location, distribution, ligand-binding affinities, interchain affinities, degradation/turnover rate, signaling, etc.

"Active" refers to those forms, fragments, or domains of UST3-LIKE1 which retain the biological and/or antigenic activities of UST3-LIKE1.

"Naturally occurring UST3-LIKE1" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to polypeptides which have been chemically modified by techniques such as ubiquitination, labeling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring UST3-LIKE1 by amino acid insertions, deletions and/or substitutions, created using recombinant DNA techniques. Guidance in determining which amino acid residues may be replaced, added, or deleted, without abolishing activities of interest may be found by comparing the sequence of the polypeptide of interest with that of related polypeptides and minimizing the number of amino acid sequence changes made in highly conserved regions.

Conservative Amino acid "substitutions" result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically while systematically making insertions, deletions, or substitutions of nucleotides in the sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. Oligopeptides comprise a stretch of amino acid residues of at least 3, 5, 10 amino acids and at most 10, 15, 25 amino acids, typically of at least 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard" expression is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (cats dogs, etc.), agricultural (cows, horses, sheep, etc.) or test species (mouse, rat, rabbit, etc.).

The nucleotide sequences encoding UST3-LIKE1 (or their complement) have numerous applications in techniques known to those skilled in the art of molecular biology. These techniques include use as hybridization probes, use in the construction of oligomers for PCR, use for chromosome and gene mapping, use in the recombinant production of UST3-LIKE1, and use in generation of antisense DNA or RNA, their chemical analogs and the like. Uses of nucleotides encoding UST3-LIKE1 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of UST3-LIKE1-encoding nucleotide sequences may be produced. Some of these will only bear minimal homology to the nucleotide sequence of the known and naturally occurring UST3-LIKE1. The invention has specifically contemplated each and every possible variation of nucleotide sequence that could be made by selecting combinations based on possible codon choices. These combinations are made in accordance with the standard triplet genetic code as applied to the nucleotide sequence of naturally occurring UST3-LIKE1, and all such variations are to be considered as being specifically disclosed.

Although the nucleotide sequences which encode UST3-LIKE1, its derivatives or its variants are preferably capable of hybridizing to the nucleotide sequence of the naturally occurring UST3-LIKE1 under stringent conditions, it may be advantageous to produce nucleotide sequences encoding UST3-LIKE1 or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding UST3-LIKE1 and/or its derivatives without altering the encoded amino acid sequence include the production of RNA transcripts having more desirable properties, such as a greater half-life, than transcripts produced from the naturally occurring sequence.

Nucleotide sequences encoding UST3-LIKE1 may be joined to a variety of other nucleotide sequences by means of well established recombinant DNA techniques. Useful nucleotide sequences for joining to UST3-LIKE1 include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for UST3-LIKE1-specific hybridization probes capable of hybridizing with naturally occurring nucleotide sequences encoding UST3-LIKE1. Such probes may also be used for the detection of similar GPCR encoding sequences and should preferably contain at least 40% nucleotide identity to UST3-LIKE1 sequence. The hybridization probes of the subject invention may be derived from the nucleotide sequence presented as SEQ ID NO: 1 or from genomic sequences including promoter, enhancers or introns of the native gene. Hybridization probes may be labeled by a variety of reporter molecules using techniques well known in the art.

It will be recognized that many deletional or mutational analogs of nucleic acid sequences for UST3-LIKE1 will be effective hybridization probes for UST3-LIKE1 nucleic acid. Accordingly, the invention relates to nucleic acid sequences that hybridize with such UST3-LIKE1 encoding nucleic acid sequences under stringent conditions.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Hybridization conditions and probes can be adjusted in well-characterized ways to achieve selective hybridization of human-derived probes.

Nucleic acid molecules that will hybridize to UST3-LIKE1 encoding nucleic acid under stringent conditions can be identified functionally. Without limitation, examples of the uses for hybridization probes include: histochemical uses such as identifying tissues that express UST3-LIKE1; measuring mRNA levels, for instance to identify a sample's tissue type or to identify cells that express abnormal levels of UST3-LIKE1; and detecting polymorphisms in UST3-LIKE1.

PCR as described in U.S. Pat. Nos. 4,683,195; 4,800,195; and 4,965,188 provides additional uses for oligonucleotides based upon the nucleotide sequence which encodes UST3-LIKE1. Such probes used in PCR may be of recombinant origin, chemically synthesized, or a mixture of both. Oligomers may comprise discrete nucleotide sequences employed under optimized conditions for identification of UST3-LIKE1 in specific tissues or diagnostic use. The same two oligomers, a nested set of oligomers, or even a degenerate pool of oligomers may be employed under less stringent conditions for identification of closely related DNAs or RNAs.

Rules for designing polymerase chain reaction ("PCR") primers are now established, as reviewed by PCR Protocols [Devlin et al]. Degenerate primers, i.e., preparations of primers that are heterogeneous at given sequence locations, can be designed to amplify nucleic acid sequences that are highly homologous to, but not identical with UST3-LIKE1. Strategies are now available that allow for only one of the primers to be required to specifically hybridize with a known sequence. For example, appropriate nucleic acid primers can be ligated to the nucleic acid sought to, be amplified to provide the hybridization partner for one of the primers. In this way, only one of the primers need be based on the sequence of the nucleic acid sought to be amplified.

PCR methods for amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known.

Other means of producing specific hybridization probes for UST3-LIKE1 include the cloning of nucleic acid sequences encoding UST3-LIKE1 or UST3-LIKE1 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is -desired can be synthesized and recombined with longer portion of an existing genomic or recombinant sequence.

Nucleotide sequences encoding UST3-LIKE1 may be used to produce a purified oligo-or polypeptide using well known methods of recombinant DNA technology. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Quantitative Determinations of Nucleic Acids

An important step in the molecular genetic analysis of human disease is often the enumeration of the copy number of a nucleis acid or the relative expression of a gene in particular tissues.

Several different approaches are currently available to make quantitative determinations of nucleic acids. Chromosome-based techniques, such as comparative genomic hybridization (CGH) and fluorescent in situ hybridization (FISH) facilitate efforts to cytogenetically localize genomic regions that are altered in tumor cells. Regions of genomic alteration can be narrowed further using loss of heterozygosity analysis (LOH), in which disease DNA is analyzed and compared with normal DNA for the loss of a heterozygous polymorphic marker. The first experiments used restriction fragment length polymorphisms (RFLPs) [Johnson et al], or hypervariable minisatellite DNA [Barnes et al]. In recent years LOH has been performed primarily using PCR amplification of microsatellite markers and electrophoresis of the radiolabeled [Jeffreys et al] or fluorescently labeled PCR products [Weber et al] and compared between paired normal and disease DNAs.

A number of other methods have also been developed to quantify nucleic acids [Gergen et al, Southern et al, Sharp et al]. More recently, PCR and RT-PCR methods have been developed which are capable of measuring the amount of a nucleic acid in a sample. One approach, for example, measures PCR product quantity in the log phase of the reaction before the formation of reaction products plateaus [Thomas et al].

A gene sequence contained in all samples at relatively constant quantity is typically utilized for sample amplification efficiency normalization. This approach, however, suffers from several drawbacks. The method requires that each sample has equal input amounts of the nucleic acid and that the amplification efficiency between samples is identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction [Maniatis et al, Becker-Andre et al, Piatak et al in BioTechniques (1993)]. The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency than the target molecule.

5' Fluorogenic Nuclease Assays

Fluorogenic nuclease assays are a real time quantitation method that uses a probe to monitor formation of amplification product. The basis for this method of monitoring the formation of amplification product is to measure continuously PCR product accumulation using a dual-labeled fluorogenic oligonucleotide probe, an approach frequently referred to in the literature simply as the "TaqMan method" [Piatak et al in Science(1993), Heid et al, Gibson et al, Holland et al].

The probe used in such assays is typically a short (about 20-25 bases) oligonucleotide that is labeled with two different fluorescent dyes. The 5' terminus of the probe is attached to a reporter dye and the 3' terminus is attached to a quenching dye, although the dyes could be attached at other locations on the probe as well. The probe is designed to have at least substantial sequence complementarity with the probe binding site. Upstream and downstream PCR primers which bind to flanking regions of the locus are added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the oligonucleotide-quencher and resulting in an increase of reporter emission intensity which can be measured by an appropriate detector.

One detector which is specifically adapted for measuring fluorescence emissions such as those created during a fluorogenic assay is the ABI 7700 or 4700 HT manufactured by Applied Biosystems, Inc. in Foster City, Calif. The ABI 7700 uses fiber optics connected with each well in a 96- or 384 well PCR tube arrangement. The instrument includes a laser for exciting the labels and is capable of measuring the fluorescence spectra intensity from each tube with continuous monitoring during PCR amplification. Each tube is reexamined every 8.5 seconds.

Computer software provided with the instrument is capable of recording the fluorescence intensity of reporter and quencher over the course of the amplification. The recorded values will then be used to calculate the increase in normalized reporter emission intensity on a continuous basis. The increase in emission intensity is plotted versus time, i.e., the number of amplification cycles, to produce a continuous measure of amplification. To quantify the locus in each amplification reaction, the amplification plot is examined at a point during the log phase of product accumulation. This is accomplished by assigning a fluorescence threshold intensity above background and determining the point at which each amplification plot crosses the threshold (defined as the threshold cycle number or Ct). Differences in threshold cycle number are used to quantify the relative amount of PCR target contained within each tube. Assuming that each reaction functions at 100% PCR efficiency, a difference of one Ct represents a two-fold difference in the amount of starting template. The fluorescence value can be used in conjunction with a standard curve to determine the amount of amplification product present.

Non-Probe-Based Detection Methods

A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green.TM. and Pico Green from Molecular Probes, Inc of Eugene, Oreg., ethidium bromide, propidium iodide, chromomycin, acridine orange, Hoechst 33258, Toto-1, Yoyo-1, DAPI (4',6-diamidino-2-phenylindole hydrochloride).

Another real time detection technique measures alteration in energy fluorescence energy transfer between fluorophors conjugated with PCR primers [Livak et al.].

Probe-Based Detection Methods

These detection methods involve some alteration to the structure or conformation of a probe hybridized to the locus between the amplification primer pair. In some instances, the alteration is caused by the template-dependent extension catalyzed by a nucleic acid polymerase during the amplification process. The alteration generates a detectable signal which is an indirect measure of the amount of amplification product formed.

For example, some methods involve the degradation or digestion of the probe during the extension reaction. These methods are a consequence of the 5'-3'nuclease activity associated with some nucleic acid polymerases. Polymerases having this activity cleave mononucleotides or small oligonucleotides from an oligonucleotide probe annealed to its complementary sequence located within the locus.

The 3' end of the upstream primer provides the initial binding site for the nucleic acid polymerase. As the polymerase catalyzes extension of the upstream primer and encounters the bound probe, the nucleic acid polymerase displaces a portion of the 5' end of the probe and through its nuclease activity cleaves mononucleotides or oligonucleotides from the probe.

The upstream primer and the probe can be designed such that they anneal to the complementary strand in close proximity to one another. In fact, the 3' end of the upstream primer and the 5' end of the probe may abut one another. In this situation, extension of the upstream primer is not necessary in order for the nucleic acid polymerase to begin cleaving the probe. In the case in which intervening nucleotides separate the upstream primer and the probe, extension of the primer is necessary before the nucleic acid polymerase encounters the 5' end of the probe. Once contact occurs and polymerization continues, the 5'-3' exonuclease activity of the nucleic acid polymerase begins cleaving mononucleotides or oligonucleotides from the 5' end of the probe. Digestion-of the probe continues until the remaining portion of the probe dissociates from the complementary strand.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product.

Probes

The labeled probe is selected so that its sequence is substantially complementary to a segment of the test locus or a reference locus. As indicated above, the nucleic acid site to which the probe binds should be located between the primer binding sites for the upstream and downstream amplification primers.

Primers

The primers used in the amplification are selected so as to be capable of hybridizing to sequences at flanking regions of the locus being amplified. The primers are chosen to have at least substantial complementarity with the different strands of the nucleic acid being amplified. When a probe is utilized to detect the formation of amplification products, the primers are selected in such that they flank the probe, i.e. are located upstream and downstream of the probe.

The primer must have sufficient length so that it is capable of priming the synthesis of extension products in the presence of an agent for polymerization. The length and composition of the primer depends on many parameters, including, for example, the temperature at which the annealing reaction is conducted, proximity of the probe binding site to that of the primer, relative concentrations of the primer and probe and the particular nucleic acid composition of the probe. Typically the primer includes 15-30 nucleotides. However, the length of the primer may be more or less depending on the complexity of the primer binding site and the factors listed above.

Labels for Probes and Primers

The labels used for labeling the probes or primers of the current invention and which can provide the signal corresponding to the quantity of amplification product can take a variety of forms. As indicated above with regard to the 5' fluorogenic nuclease method, a fluorescent signal is one signal which can be measured. However, measurements may also be made, for example, by monitoring radioactivity, colorimetry, absorption, magnetic parameters, or enzymatic activity. Thus, labels which can be employed include, but are not limited to, fluorophors, chromophores, radioactive isotopes, electron dense reagents, enzymes, and ligands having specific binding partners (e.g., biotin-avidin).

Monitoring changes in fluorescence is a particularly useful way to monitor the accumulation of amplification products. A number of labels useful for attachment to probes or primers are commercially available including fluorescein and various fluorescein derivatives such as FAM, HEX, TET and JOE (all which are available from Applied Biosystems, Foster City, Calif.); lucifer yellow, and coumarin derivatives.

Labels may be attached to the probe or primer using a variety of techniques and can be attached at the 5' end, and/or the 3' end and/or at an internal nucleotide. The label can also be attached to spacer arms of various sizes which are attached to the probe or primer. These spacer arms are useful for obtaining a desired distance between multiple labels attached to the probe or primer.

In some instances, a single label may be utilized; whereas, in other instances, such as with the 5' fluorogenic nuclease assays for example, two or more labels are attached to the probe. In cases wherein the probe includes multiple labels, it is generally advisable to maintain spacing between the labels which is sufficient to permit separation of the labels during digestion of the probe through the 5'-3' nuclease activity of the nucleic acid polymerase.

Patients Exhibiting Symptoms of Disease

A number of diseases are associated with changes in the copy number of a certain gene. For patients having symptoms of a disease, the real-time PCR method can be used to determine if the patient has copy number alterations which are known to be linked with diseases that are associated with the symptoms the patient has.

UST3-LIKE1 Expression

UST3-LIKE1 Fusion Proteins

Fusion proteins are useful for generating antibodies against UST3-LIKE1 amino acid sequences and for use in various assay systems. For example, fusion proteins can be used to identify proteins which interact with portions of UST3-LIKE1peptide. Protein affinity chromatography or library-based assays for protein-protein interactions, such as the yeast two-hybrid or phage display systems, can be used for this purpose. Such methods are well known in the art and also can be used as drug screens.

A UST3-LIKE1 fusion protein comprises two polypeptide segments fused together by means of a peptide bond. The first polypeptide segment can comprise at least 54, 75, 100, 125, 139, 150, 175, 200, 225, 250, or 275 contiguous amino acids of SEQ ID NO:2 or of a biologically active variant, such as those described above. The first polypeptide segment also can comprise full-length UST3-LIKE1.

The second polypeptide segment can be a fill-length protein or a protein fragment. Proteins commonly used in fusion protein construction include, but are not limited to β galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyl-transferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, herpes simplex virus (HSV) BP16 protein fusions and G-protein fusions (for example G(alpha) 16, Gs, Gi). A fusion protein also can be engineered to contain a cleavage site located adjacent to the UST3-LIKE1.

Preparation of Polynucleotides

A naturally occurring UST3-LIKE1 polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated UST3-LIKE1 polynucleotides. For example, restriction enzymes and probes can be used to isolate polynucleotide fragments which comprises UST3-LIKE1 nucleotide sequences. Isolated polynucleotides are in preparations which are free or at least 70, 80, or 90% free of other molecules.

UST3-LIKE1 cDNA molecules can be made with standard molecular biology techniques, using UST3-LIKE1 mRNA as a template. UST3-LIKE1 cDNA molecules can thereafter be replicated using molecular biology techniques known in the art. An amplification technique, such as PCR, can be used to obtain additional copies of polynucleotides of the invention, using either human genomic DNA or cDNA as a template.

Alternatively, synthetic chemistry techniques can be used to synthesizes UST3-LIKE1 polynucleotides. The degeneracy of the genetic code allows alternate nucleotide sequences to be synthesized which will encode UST3-LIKE1 having, for example, an amino acid sequence shown in SEQ ID NO:2 or a biologically active variant thereof.

Extending Polynucleotides

Various PCR-based methods can be used to extend nucleic acid sequences encoding human UST3-LIKE1, for example to detect upstream sequences of the UST3-LIKE1 gene such as promoters and regulatory elements. For example, restriction-site PCR uses universal primers to retrieve unknown sequence adjacent to a known locus. Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region. Primers can be designed using commercially available software, such as OLIGO 4.06 Primer Analysis software (National Biosciences Inc., Plymouth, Minn.), to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA. In this method, multiple restriction enzyme digestions and ligations also can be used to place an engineered double-stranded sequence into an unknown fragment of the DNA molecule before performing PCR.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate equipment and software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

UST3-LIKE1 can be obtained, for example, by purification from human cells, by expression of UST3-LIKE1 polynucleotides, or by direct chemical synthesis.

Protein Purification

UST3-LIKE1 can be purified from any human cell which expresses the transporter, including those which have been transfected with expression constructs which express UST3-LIKE1. A purified UST3-LIKE1 is separated from other compounds which normally associate with UST3-LIKE1 in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

Expression of UST3-LIKE1 Polynucleotides

To express UST3-LIKE1, UST3-LIKE1 polynucleotide can be inserted into an expression vector which contains the necessary elements for the transcription and translation of the inserted coding sequence. Methods which are well known to those skilled in the art can be used to construct expression vectors containing sequences encoding UST3-LIKE1 and appropriate transcriptional and translational control elements. These methods include in vitro recombinant DNA techniques, synthetic techniques, and in vivo genetic recombination [Devlin et al., Science, (1990)].

A variety of expression vector/host systems can be utilized to contain and express sequences encoding UST3-LIKE1. These include, but are not limited to, micro-organisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example; when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding UST3-LIKE1, vectors based on SV40 or EBV can be used with an appropriate selectable marker.

Bacterial and Yeast Expression Systems

In bacterial systems, a number of expression vectors can be selected. For example, when a large quantity of UST3-LIKE1 is needed for the induction of antibodies, vectors which direct high level expression of fusion proteins that are readily-purified can be used. Such vectors include, but are not limited to, multifunctional *E. coli* cloning and expression vectors such as BLUESCRIPT (Stratagene). In a BLUESCRIPT vector, a sequence encoding UST3-LIKE1 can be ligated into the vector in frame with sequences for the amino-terminal Met and the subsequent 7 residues of β-galactosidase so that a hybrid protein is produced. pIN vectors or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

Plant and Insect Expression Systems

If plant expression vectors are used, the expression of sequences encoding UST3-LIKE1 can be driven by any of a number of promoters. For example, viral promoters such as the 35S and 19S promoters of CaMV can be used alone or in combination with the omega leader sequence from TMV [Scott et al. (1990)]. Alternatively, plant promoters such as the small subunit of RUBISCO or heat shock promoters can be used [Takamatsu et al. (1987)]. These constructs can be introduced into plant cells by direct DNA transformation or by pathogen-mediated transfection.

An insect system also can be used to express UST3-LIKE1. For example, in one such system *Autographa californica* nuclear polyhedrosis virus (AcNPV) is used as a vector to express foreign genes in *Spodoptera frugiperda* cells or in *Trichoplusia* larvae. Sequences encoding UST3-LIKE1 can be cloned into a non-essential region of the virus, such as the polyhedrin gene, and placed under control of the polyhedrin promoter. Successful insertion of UST3-LIKE1 will render the polyhedrin gene inactive and produce recombinant virus lacking coat protein. The recombinant viruses can then be used to infect *S. frugiperda* cells or *Trichoplusia* larvae in which UST3-LIKE1 can be expressed [Fodor et al., (1993)].

Mammalian Expression Systems

A number of viral-based expression systems can be used to express UST3-LIKE1 in mammalian host cells. For example, if an adenovirus is used as an expression vector, sequences encoding UST3-LIKE1 can be ligated into an adenovirus transcription/translation complex comprising the late promoter and tripartite leader sequence. Insertion in a non-essential E1 or E3 region of the viral genome can be used to obtain a viable virus which is capable of expressing UST3-LIKE1 in infected host cells [Engelhard et al. (1994)]. If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles). Specific initiation signals also can be used to achieve more efficient translation of sequences encoding UST3-LIKE1. Such signals include the ATG initiation codon and adjacent sequences. In cases where sequences encoding UST3-LIKE1, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic.

Host Cells

A host cell strain can be chosen for its ability to modulate the expression of the inserted sequences or to process the expressed UST3-LIKE1 in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express UST3-LIKE1 can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells which successfully express the introduced UST3-LIKE1 sequences. Resistant clones of stably transformed cells can be proliferated using tissue culture techniques appropriate to the cell type. Any number of selection systems can be used to recover transformed cell lines. These include, but are not limited to, the herpes simplex virus thymidine kinase [Logan & Shenck, (1984)] and adenine phosphoribosyltransferase [Wigler et al., (1977)] genes which can be employed in tk⁻ or aprt⁻ cells, respectively. Also, antimetabolite, antibiotic, or herbicide resistance can be used as the basis for selection. For example, dhfr confers resistance to methotrexate [Lowy et al., (1980)], npt confers resistance to the aminoglycosides, neomycin and G-418 [Wigler et al., Proc. Natl. Acad. Sci. (1980)], and als and pat confer resistance to chlorsulfuron and phosphinotricin acetyltransferase, respectively [Colbere-Garapin et al., (1981)]. Additional selectable genes have been described. For example, trpB allows cells to utilize indole in place of tryptophan, or hisD, which allows cells to utilize histinol in place of histidine [Murray et al., (1992)]. Visible markers such as anthocyanins, β-glucuronidase and its substrate GUS, and luciferase and its substrate luciferin, can be used to identify transformants and to quantify the amount of transient or stable protein expression attributable to a specific vector system Detecting Polypeptide Expression Although the presence of marker gene expression suggests that a UST3-LIKE1 polynucleotide is also present, its presence and expression may need to be confirmed. For example, if a sequence encoding UST3-LIKE1 is inserted within a marker gene sequence, transformed cells containing sequences which encode UST3-LIKE1 can be identified by the absence of marker gene function. Alternatively, a marker gene can be placed in tandem with a sequence encoding UST3-LIKE1 under the control of a single promoter. Expression of the marker gene in response to induction or selection usually indicates expression of UST3-LIKE1 polynucleotide.

Alternatively, host cells which contain a UST3-LIKE1 polynucleotide and which express UST3-LIKE1 can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding UST3-LIKE1 can be detected by DNA-DNA or DNA-RNA hybridization or amplification using probes or fragments or fragments of polynucleotides encoding UST3-LIKE1. Nucleic acid amplification-based assays involve the use of oligonucleotides selected from sequences encoding UST3-LIKE1 to detect transformants which contain a UST3-LIKE1 polynucleotide.

A variety of protocols for detecting and measuring the expression of UST3-LIKE1, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on UST3-LIKE1 can be used, or a competitive binding assay can be employed [Hartman & Mulligan, (1988), Hamptonet al.,(1990)].

A wide variety of labels and conjugation techniques are known by those skilled in the art and can be used in various nucleic acid and amino acid assays. Means for producing labeled hybridization or PCR probes for detecting sequences related to polynucleotides encoding UST3-LIKE1 include oligolabeling, nick translation, end-labeling, or PCR amplification using a labeled nucleotide. Alternatively, sequences encoding UST3-LIKE1 can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding UST3-LIKE1 can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode UST3-LIKE1 can be designed to contain signal sequences which direct secretion of soluble UST3-LIKE1 through a prokaryotic or eukaryotic cell membrane or which direct the membrane insertion of membrane-bound UST3-LIKE1.

As discussed above, other constructions can be used to join a sequence encoding UST3-LIKE1 to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor XA or enterokinase nitrogen, San Diego, Calif.) between the purification domain and UST3-LIKE1 also can be used to facilitate purification. One such expression vector provides for expression of a fusion protein containing UST3-LIKE1 and 6 histidine residues preceding a thioredoxin or an enterokinase cleavage site. The histidine residues facilitate purification by IMAC (immobilized metal ion affinity chromatography) Maddox et al., (1983)], while the enterokinase cleavage site provides a means for purifying UST3-LIKE1 from the fusion protein [Porath et al., (1992)].

Chemical Synthesis

Sequences encoding UST3-LIKE1 can be synthesized, in whole or in part, using chemical methods well known in the art [Kroll et al. (1993), Caruthers et al., (1980)]. Alternatively, UST3-LIKE1 itself can be produced using chemical methods to synthesize its amino acid sequence, such as by direct peptide synthesis using solid-phase techniques [Horn et al., (1980); Merrifield et al., (1963)]. Protein synthesis can either be performed using manual techniques or by automation. Automated synthesis can be achieved, for example, using Applied Biosystems 431A Peptide Synthesizer (Perkin Elmer). Optionally, fragments of UST3-LIKE1 can be separately synthesized and combined using chemical methods to produce a full-length molecule.

The newly synthesized peptide can be substantially purified by preparative high performance liquid chromatography. The composition of a synthetic UST3-LIKE1 can be confirmed by amino acid analysis or sequencing. Additionally, any portion of the amino acid sequence of UST3-LIKE1 can be altered during direct synthesis and/or combined using chemical methods with sequences from other proteins to produce a variant polypeptide or a fusion protein.

Production of Altered Polypeptides

As will be understood by those of skill in the art, it may be advantageous to produce UST3-LIKE1-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences referred to herein can be engineered using methods generally known in the art to alter UST3-LIKE1-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of UST3-LIKE1. "Antibody" as used herein includes intact immunoglobulin molecules, as well as fragments thereof, such as Fab, F(ab')$_2$, and Fv, which are capable of binding an epitope of UST3-LIKE1. Typically, at least 6, 8, 10, or 12 contiguous amino acids are required to form an epitope. However, epitopes which involve non-contiguous amino acids may require more, e.g., at least 15, 25, or 50 amino acid. An antibody which specifically binds to an epitope of UST3-LIKE1 can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to UST3-LIKE1 provides a detection signal at least 5-, 10-, or 20-fold higher than a detection signal provided with other proteins when used in an immunochemical assay. Preferably, antibodies which specifically bind to UST3-LIKE1 do not detect other proteins in immunochemical assays and can immunoprecipitate UST3-LIKE1 from solution.

UST3-LIKE1 can be used to immunize a mammal, such as a mouse, rat, rabbit, guinea pig, monkey, or human, to produce polyclonal antibodies. If desired, UST3-LIKE1 can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to UST3-LIKE1 can be prepared using any technique which provides for the production of antibody molecules by continuous cell lines in culture. These techniques include, but are not limited to, the hybridoma technique, the human B-cell hybridoma technique, and the EBV-hybridoma technique [Roberge et al., (1995); Kohler et al., (1985); Kozbor et al., (1985); Cote et al., (1983)].

In addition, techniques developed for the production of "chimeric antibodies," the splicing of mouse antibody genes to human antibody genes to obtain a molecule with appropriate antigen specificity and biological activity, can be used [Cole et al. (1984); Morrison et al. (1984); Neuberger et al. (1984)]. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Antibodies which specifically bind to UST3-LIKE1 can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to UST3-LIKE1. Antibodies with related specificity, but of distinct idiotypic composition, can be generated by chain shuffling from random combinatorial immunoglobin libraries [Takeda et al., (1985)]. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology [Burton et al. (1991); Verhaar et al. (1995)].

Antibodies which specifically bind to UST3-LIKE1 also can be produced by inducing in vivo production in the lymphocyte population or by screening immunoglobulin libraries or panels of highly specific binding reagents. Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which UST3-LIKE1 is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of UST3-LIKE1 gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of UST3-LIKE1 gene expression can be obtained by designing antisense oligonucleotides which will form duplexes to the control, 5', or regulatory regions of the UST3-LIKE1 gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature [Nicholls et al. (1993)]. An antisense oligonucleotide also can be designed to block translation of mRNA by preventing the transcript from binding to ribosomes.

Precise complementarity is not required for successful complex formation between an antisense oligonucleotide and the complementary sequence of a UST3-LIKE1 polynucleotide. Antisense oligonucleotides which comprise, for example, 2, 3, 4, or 5 or more stretches of contiguous nucleotides which are precisely complementary to a UST3-LIKE1 polynucleotide, each separated by a stretch of contiguous nucleotides which are not complementary to adjacent UST3-LIKE1 nucleotides, can provide sufficient targeting specificity for UST3-LIKE1 mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular UST3-LIKE1 polynucleotide sequence. Antisense oligonucleotides can be modified without affecting their ability to hybridize to a UST3-LIKE1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art [Gee et al. (1994); Agrawal et al. (1992); Uhlmann et al. (1990)].

Ribozymes

Ribozymes are RNA molecules with catalytic activity Uhlmann et al. (1987); Cech et al. (1987), (1990), (1992)]. Ribozymes can be used to inhibit gene function by cleaving an RNA sequence, as is known in the art (U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a UST3-LIKE1 polynucleotide can be used to generate ribozymes which will specifically bind to mRNA transcribed from a UST3-LIKE1 polynucleotide. Methods of designing and constructing ribozymes which can cleave other RNA molecules in trans in a highly sequence specific manner have been developed and described in the art [Couture & Stinchcomb (1996)]. For example, the cleavage activity of ribozymes can be targeted to specific RNAs by engineering a discrete "hybridization" region into the ribozyme. The hybridization region contains a sequence complementary to the target RNA and thus specifically hybridizes with the.

Specific ribozyme cleavage sites within a UST3-LIKE1 RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate UST3-LIKE1 RNA targets also can be evaluated by testing accessibility to hybridization with complementary oligonucleotides using ribonuclease protection assays. The nucleotide sequences shown in SEQ ID NO:1 and its complement provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease UST3-LIKE1 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells (U.S. Pat. No. 5,641,673). Ribozymes also can be engineered to provide an additional level of regulations so that destruction of mRNA occurs only when both a ribozyme and a target gene are induced in the cells.

Screening/Screening Assays

Regulators

Regulators as used herein, refers to UST3-LIKE1 agonists and UST3-LIKE1 antagonists. Agonists of UST3-LIKE1 are molecules which, when bound to UST3-LIKE1, increase or prolong the activity of UST3-LIKE1. Agonists of UST3-LIKE1 include proteins, nucleic acids, carbohydrates, small molecules, or any other molecule which activate UST3-LIKE1. Antagonists of UST3-LIKE1 are molecules which, when bound to UST3-LIKE1, decrease the amount or the duration of the activity of UST3-LIKE1. Antagonists include proteins, nucleic acids, carbohydrates, antibodies, small molecules, or any other molecule which decrease the activity of UST3-LIKE1.

The term "modulate," as it appears herein, refers to a change in the activity of UST3-LIKE1. For example, modulation may cause an increase or a decrease in protein activity, binding characteristics, or any other biological, functional, or immunological properties of UST3-LIKE1.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

The invention provides methods (also referred to herein as "screening assays") for identifying compounds which can be used for the treatment of gastrointestinal and liver diseases, metabolic diseases, hematological disorders, respiratory diseases, neurological disorders, urological disorders and cardiovascular diseases. The methods entail the identification of candidate or test compounds or agents (e.g., peptides, peptidomimetics, small molecules or other molecules) which bind to UST3-LIKE1 and/or have a stimulatory or inhibitory effect on the biological activity of UST3-LIKE1 or its expression and then determining which of these compounds have an effect on symptoms or diseases regarding the gastrointestinal and liver diseases, metabolic diseases, hematological disorders, respiratory diseases, neurological disorders, urological disorders and cardiovascular diseases in an in vivo assay.

Candidate or test compounds or agents which bind to UST3-LIKE1 and/or have a stimulatory or inhibitory effect on the activity or the expression of UST3-LIKE1 are identified either in assays that employ cells which express UST3-LIKE1 on the cell surface (cell-based assays) or in assays with isolated UST3-LIKE1 (cell-free assays). The various assays can employ a variety of variants of UST3-LIKE1 (e.g., full-length UST3-LIKE1, a biologically active fragment of UST3-LIKE1, or a fusion protein which includes all or a portion of UST3-LIKE1). Moreover, UST3-LIKE1 can be derived from any suitable mammalian species (e.g., human UST3-LIKE1, rat UST3-LIKE1 or murine UST3-LIKE1). The assay can be a binding assay entailing direct or indirect measurement of the binding of a test compound or a known UST3-LIKE1 ligand to UST3-LIKE1. The assay can also be an activity assay entailing direct or indirect measurement of the activity of UST3-LIKE1. The assay can also be an expression assay entailing direct or indirect measurement of the expression of UST3-LIKE1 mRNA or UST3-LIKE1 protein. The various screening assays are combined with an in vivo assay entailing measuring the effect of the test compound on the symtoms of a gastrointestinal and liver diseases, metabolic diseases, hematological disorders, respiratory diseases, neurological disorders, urological disorders and cardiovascular diseases.

In one embodiment, the invention provides assays for screening candidate or test compounds which bind to or modulate the activity of a membrane-bound (cell surface expressed) form of UST3-LIKE1. Such assays can employ full-length UST3-LIKE1, a biologically active fragment of UST3-LIKE1, or a fusion protein which includes all or a portion of UST3-LIKE1. As described in greater detail below, the test compound can be obtained by any suitable means, e.g., from conventional compound libraries. Determining the ability of the test compound to bind to a membrane-bound form of UST3-LIKE1 can be accomplished, for example, by coupling the test compound with a radioisotope or enzymatic label such that binding of the test compound to the UST3-LIKE1-expressing cell can be measured by detecting the labeled compound in a complex. For example, the test compound can be labeled with . . . $^{125}$I, . . . $^{35}$S, . . . $^{14}$C, or . . . $^{3}$H, either directly or indirectly, and the radioisotope detected by direct counting of radioemmission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

In a competitive binding format, the assay comprises contacting UST3-LIKE1-expressing cell with a known compound which binds to UST3-LIKE1 to form an assay mixture, contacting the assay mixture with a test compound, and determining the ability of the test compound to interact with the UST3-LIKE1-expressing cell, wherein determining the ability of the test compound to interact with the UST3-LIKE1-expressing cell comprises determining the ability of the test compound to preferentially bind the UST3-LIKE1-expressing cell as compared to the known compound.

In another embodiment, the assay is a cell-based assay comprising contacting a cell expressing a membrane-bound form of UST3-LIKE1 (e.g., full-length UST3-LIKE1, a biologically active fragment of UST3-LIKE1, or a fusion protein which includes all or a portion of UST3-LIKE1) expressed on the cell surface with a test compound and determining the ability of the test compound to modulate (e.g., stimulate or inhibit) the activity of the membrane-bound form of UST3-LIKE1. Determining the ability of the test compound to modulate the activity of the membrane-bound form of UST3-LIKE1 can be accomplished by any method suitable for measuring the activity of UST3-LIKE1. The activity of a transporter can be measured in a number of ways, not all of which are suitable for any given transporter.

Determining the ability of the test compound to modulate the activity of UST3-LIKE1 can be accomplished, for example, by determining the ability of UST3-LIKE1 to bind to or interact with a target molecule. The target molecule can be a molecule with which UST3-LIKE1 binds or interacts with in nature, for example, a molecule on the surface of a cell which expresses UST3-LIKE1, a molecule on the surface of a second cell, a molecule in the extracellular milieu, a molecule associated with the internal surface of a cell membrane or a cytoplasmic molecule. The target molecule can be a component of a signal transduction pathway which facilitates transduction of an extracellular signal (e.g., a signal generated by binding of a UST3-LIKE1 ligand, through the cell membrane and into the cell. The target molecule can be, for example, a second intracellular protein which has catalytic activity or a protein which facilitates the association of downstream signaling molecules with UST3-LIKE1.

Determining the ability of UST3-LIKE1 to bind to or interact with a target molecule can be accomplished by one of the methods described above for determining direct binding. In one embodiment, determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response.

The present invention also includes cell-free assays. Such assays involve contacting a form of UST3-LIKE1 (e.g., full-length UST3-LIKE1, a biologically active fragment of UST3-LIKE1, or a fusion protein comprising all or a portion of UST3-LIKE1) with a test compound and determining the ability of the test compound to bind to UST3-LIKE1. Binding of the test compound to UST3-LIKE1 can be determined either directly or indirectly as described above. In one embodiment, the assay includes contacting UST3-LIKE1 with a known compound which binds UST3-LIKE1 to form an assay mixture, contacting the assay mixture with a test compound, and determining the ability of the test compound to interact with UST3-LIKE1, wherein determining the ability of the test compound to interact with UST3-LIKE1 comprises determining the ability of the test compound to preferentially bind to UST3-LIKE1 as compared to the known compound.

The cell-free assays of the present invention are amenable to use of either a membrane-bound form of UST3-LIKE1 or a soluble fragment thereof. In the case of cell-free assays comprising the membrane-bound form of the polypeptide, it may be desirable to utilize a solubilizing agent such that the membrane-bound form of the polypeptide is maintained in solution. Examples of such solubilizing agents include but are not limited to non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In various embodiments of the above assay methods of the present invention, it may be desirable to immobilize UST3-LIKE1 (or a UST3-LIKE1 target molecule) to facilitate separation of complexed from uncomplexed forms of one or both of the proteins, as well as to accommodate automation of the assay. Binding of a test compound to UST3-LIKE1, or interaction of UST3-LIKE1 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or UST3-LIKE1, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of UST3-LIKE1 can be determined using standard techniques.

Other techniques for immobilizing proteins on matrices can also be used in the screening assays of the invention. For example, either UST3-LIKE1 or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated plates (Pierce Chemical). Alternatively, antibodies reactive with UST3-LIKE1 or target molecules but which do not interfere with binding of the polypeptide of the invention to its target molecule can be derivatized to the wells of the plate, and unbound target or polypeptidede of the invention trapped in the wells by antibody conjugation. Methods for detecting such complexes, in addition to those described above for the GST-immobilized complexes, include immunodetection of complexes using antibodies reactive with UST3-LIKE1 or target molecule, as well as enzyme-linked assays which rely on detecting an enzymatic activity associated with UST3-LIKE1 or target molecule.

The screening assay can also involve monitoring the expression of UST3-LIKE1. For example, regulators of expression of UST3-LIKE1 can be identified in a method in which a cell is contacted with a candidate compound and the expression of UST3-LIKE1 protein or mRNA in the cell is determined. The level of expression of UST3-LIKE1 protein or mRNA the presence of the candidate compound is compared to the level of expression of UST3-LIKE1 protein or mRNA in the absence of the candidate compound. The candidate compound can then be identified as a regulator of expression of UST3-LIKE1 based on this comparison. For example, when expression of UST3-LIKE1 protein or mRNA protein is greater (statistically significantly greater) in the presence of the candidate compound than in its absence, the candidate compound is identified as a stimulator of UST3-LIKE1 protein or mRNA expression. Alternatively, when expression of UST3-LIKE1 protein or mRNA is less (statistically significantly less) in the presence of the candidate compound than in its absence, the candidate compound is identified as an inhibitor of UST3-LIKE1 protein or mRNA expression. The level of UST3-LIKE1 protein or mRNA expression in the cells can be determined by methods described below.

Binding Assays

For binding assays, the test compound is preferably a small molecule which binds to and occupies the active site of UST3-LIKE1 transporter polypeptide, thereby making the ligand binding site inaccessible to substrate such that normal biological activity is prevented. Examples of such small molecules include, but are not limited to, small peptides or peptide-like molecules. Potential ligands which bind to a polypeptide of the invention include, but are not limited to, the natural ligands of known UST3-LIKE1 transporter and analogues or derivatives thereof.

In binding assays, either the test compound or the UST3-LIKE1 transporter polypeptide can comprise a detectable label, such as a fluorescent, radioisotopic, chemiluminescent, or enzymatic label, such as horseradish peroxidase, alkaline phosphatase, or luciferase. Detection of a test compound which is bound to UST3-LIKE1 transporter polypeptide can then be accomplished, for example, by direct counting of radioemmission, by scintillation counting, or by determining conversion of an appropriate substrate to a detectable product. Alternatively, binding of a test compound to a UST3-LIKE1 transporter polypeptide can be determined without labeling either of the interactants. For example, a microphysiometer can be used to detect binding of a test compound with a UST3-LIKE1 transporter polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and UST3-LIKE1 [Haseloff et al. (1988)].

Determining the ability of a test compound to bind to UST3-LIKE1 also can be accomplished using a technology such as real-time Bimolecular Interaction Analysis (BIA) [McConnell et al. (1992), Sjolander & Urbaniczky (1991)].

BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a UST3-LIKE1-like polypeptide can be used as a "bait protein" in a two-hybrid assay or three-hybrid assay [Szabo et al., (1995); Zervos et al. (1993); Madura et al. (1993); Bartel et al. (1993)]; U.S. Pat. No. 5,283,317), to identify other proteins which bind to or interact with UST3-LIKE1 and modulate its activity.

The two-hybrid system is based on the modular nature of most transcription factors, which consist of separable DNA-binding and activation domains. Briefly, the assay utilizes two different DNA constructs. For example, in one construct, polynucleotide encoding UST3-LIKE1 can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with UST3-LIKE1.

It may be desirable to immobilize either the UST3-LIKE1 (or polynucleotide) or the test compound to facilitate separation of the bound form from unbound forms of one or both of the interactants, as well as to accommodate automation of the assay. Thus, either the UST3-LIKE1-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach UST3-LIKE1-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to UST3-LIKE1 (or a polynucleotide encoding for UST3-LIKE1) can be accomplished in any vessel suitable for containing the reactants. Examples of such vessels include microtiter plates, test tubes, and microcentrifuge tubes.

In one embodiment, UST3-LIKE1 is a fusion protein comprising a domain that allows binding of UST3-LIKE1 to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed UST3-LIKE1; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either UST3-LIKE1 (or a polynucleotide encoding UST3-LIKE1) or a test compound can be immobilized utilizing conjugation of biotin and streptavidin. Biotinylated UST3-LIKE1 (or a polynucleotide encoding biotinylated UST3-LIKE1) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated plates (Pierce Chemical). Alternatively, antibodies which specifically bind to UST3-LIKE1, polynucleotide, or a test compound, but which do not interfere with a desired binding site, such as the active site of UST3-LIKE1, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to UST3-LIKE1 transporter polypeptide or test compound, enzyme-linked assays which rely on detecting an activity of UST3-LIKE1 transporter polypeptide, and SDS gel electrophoresis under non-reducing conditions.

Screening for test compounds which bind to a UST3-LIKE1 transporter polypeptide or polynucleotide also can be carried out in an intact cell. Any cell which comprises a UST3-LIKE1 transporter polypeptide or polynucleotide can be used in a cell-based assay system. A UST3-LIKE1 transporter polynucleotide can be naturally occurring in the cell or can be introduced using techniques such as those described above. Binding of the test compound to UST3-LIKE1 or a polynucleotide encoding UST3-LIKE1 is determined as described above.

Functional Assays

Test compounds can be tested for the ability to increase or decrease UST3-LIKE1 activity of a UST3-LIKE1 transporter polypeptide. The UST3-LIKE1 activity can be measured, for example, using methods described in the specific examples, below. UST3-LIKE1 activity can be measured after contacting either a purified UST3-LIKE1, a cell membrane preparation, or an intact cell with a test compound. A test compound which decreases UST3-LIKE1 activity by at least about 10, preferably about 50, more preferably about 75, 90, or 100% is identified as a potential agent for decreasing UST3-LIKE1 activity. A test compound which increases UST3-LIKE1 activity by at least about 10, preferably about 50, more preferably about 75, 90, or 100% is identified as a potential agent for increasing UST3-LIKE1 activity.

One such screening procedure involves the use of melanophores which are transfected to express UST3-LIKE1. Such a screening technique is described in PCT WO 92/01810 published Feb. 6, 1992. Thus, for example, such an assay may be employed for screening for a compound which inhibits activation of the transporter polypeptide of the present invention by contacting the melanophore cells which encode the transporter with both the transporter ligand and a compound to be screened. Inhibition of the signal generated by the ligand indicates that a compound is a potential antagonist for the transporter, i.e., inhibits activation of the transporter. The screen may be employed for identifying a compound which activates the transporter by contacting such cells with compounds to be screened and determining whether each compound generates a signal, i.e., activates the transporter.

Other screening techniques include the use of cells which express UST3-LIKE1 (for example, transfected CHO cells) in a system which measures extracellular pH changes caused by transporter activation [Iwabuchi et al. (1993)]. For example, compounds may be contacted with a cell which expresses the transporter polypeptide of the present invention and a second messenger response, e.g., signal transduction or pH changes, can be measured to determine whether the potential compound activates or inhibits the transporter. Another such screening technique involves introducing RNA encoding UST3-LIKE1 into *Xenopus* oocytes to transiently express the transporter. The transporter oocytes can then be contacted with the transporter ligand and a compound to be screened, followed by detection of inhibition or activation of a calcium signal in the case of screening for compounds which are thought to inhibit activation of the transporter.

Gene Expression

In another embodiment, test compounds which increase or decrease UST3-LIKE1 gene expression are identified. As used herein, the term "correlates with expression of a "polynucleotide" indicates that the detection of the presence of nucleic acids, the same or related to a nucleic acid sequence encoding UST3-LIKE1, by northern analysis or relatime PCR is indicative of the presence of nucleic acids encoding UST3-LIKE1 in a sample, and thereby correlates with expression of the transcript from the polynucleotide encoding UST3-LIKE1. The term "microarray," as used herein, refers to an array of distinct polynucleotides or oligonucleotides arrayed on a substrate, such as paper, nylon or any other type of membrane, filter, chip, glass slide, or any other suitable solid support. A UST3-LIKE1 polynucleotide is contacted with a test compound, and the expression of an RNA or polypeptide product of UST3-LIKE1 polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of UST3-LIKE1 mRNA or polypeptide expression in the cells can be determined by methods well known in the art for detecting mRNA or polypeptide. Either qualitative or quantitative methods can be used. The presence of polypeptide products of UST3-LIKE1 transporter polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into UST3-LIKE1.

Such screening can be carried out either in a cell-free assay system or in an intact cell. Any cell which expresses UST3-LIKE1 polynucleotide can be used in a cell-based assay system. The UST3-LIKE1 polynucleotide can be naturally occurring in the cell or can be introduced using techniques such as those described above. Either a primary culture or an established cell line can be used.

Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds [Lam et al. (1997)].

Examples of methods for the synthesis of molecular libraries can be found in the art [Lam et al. (1997); DeWitt et al. (1993); Erb. et al. (1994); Zuckermann et al. (1994); Cho et al. (1993); Carrell et al. (1994) Angew. Chem. Int. Ed. Engl. 33:2059]. Libraries of compounds may be presented in solution [Carrell et al. (1994), Angew. Chem. Int. Ed. Engl. 33: 2061; Gallop et al. (1994)] or on beads [Houghten et al. (1992)], chips [Cull et al. (1992)], bacteria (U.S. Pat. No. 5,223,409), spores (U.S. Pat. Nos. 5,571,698; 5,403,484; and 5,223,409), plasmids [Coruzzi et al. (1984)] or phage [Nagarenko et al. (1997); Fehci al. [1991]; Cwirla et al. (1990); Devlin et al. (1990); Sambrook et al. (1989)].

Modeling of Regulators

Computer modeling and searching technologies permit identification of compounds, or the improvement of already identified compounds, that can modulate UST3-LIKE1 expression or activity. Having identified such a compound or composition, the active sites or regions are identified. Such active sites might typically be ligand binding sites, such as the interaction domain of the ligand with UST3-LIKE1. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential UST3-LIKE1 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Therapeutic Indications and Methods

It was found by the present applicant that UST3-LIKE1 is expressed in different human tissues.

Gastrointestinal and Liver Diseases

The human UST3 like protein 1 is highly expressed in the following tissues of the gastroenterological system: fetal liver, liver, liver liver cirrhosis, liver tumor, HEP G2 cells. The expression in the above mentioned tissues and in particular the differential expression between diseased tissue liver liver cirrhosis and healthy tissue liver, between diseased tissue liver tumor and healthy tissue liver, between diseased tissue HEP G2 cells and healthy tissue liver demonstrates that the human UST3 like protein 1 or mRNA can be utilized to diagnose of gastroenterological disorders. Additionally the activity of the human UST3 like protein 1 can be modulated to treat gastroenterological disorders.

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise but are not limited to 1) disorders of the esophagus like achalasia, vigoruos achalasia, dysphagia, cricopharyngeal incoordination, pre-esophageal dysphagia, diffuse esophageal spasm, globus sensation, Barrett's metaplasia, gastroesophageal reflux, 2) disorders of the stomach and duodenum like functional dyspepsia, inflammation of the gastric mucosa, gastritis, stress gastritis, chronic erosive gastritis, atrophy of gastric glands, metaplasia of gastric tissues, gastric ulcers, duodenal ulcers, neoplasms of the stomach, 3) disorders of the pancreas like acute or chronic pancreatitis, insufficiency of the exocrinic or endocrinic tissues of the pancreas like steatorrhea, diabetes, neoplasms of the exocrine or endocrine pancreas like 3.1) multiple endocrine neoplasia syndrome, ductal adenocarcinoma, cystadenocarcinoma, islet cell tumors, insulinoma, gastrinoma, carcinoid tumors, glucagonoma, Zollinger-Ellison syndrome, Vipoma syndrome, malabsorption syndrome, 4) disorders of the bowel like chronic inflammatory diseases of the bowel, Crohn's disease, ileus, diarrhea and constipation, colonic inertia, megacolon, malabsorption syndrome, ulcerative colitis, 4.1) functional bowel disorders like irritable bowel syndrome, 4.2) neoplasms of the bowel like familial polyposis, adenocarcinoma, primary malignant lymphoma, carcinoid tumors, Kaposi's sarcoma, polyps, cancer of the colon and rectum.

Liver diseases comprise primary or secondary, acute or chronic diseases or injury of the liver which may be acquired or inherited, benign or malignant, and which may affect the liver or the body as a whole. They comprise but are not limited to disorders of the bilirubin metabolism, jaundice, syndroms of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, liver diseases due to alcohol, alcoholic hepatitis or cirrhosis, fibrosis and cirrhosis, fibrosis and cirrhosis of the liver due to inborn errors of metabolism or exogenous substances, storage diseases, syndromes of Gaucher's, Zellweger's, Wilson's—disease, acute or chronic hepatitis, viral hepatitis and its variants, inflammatory conditions of the liver due to viruses, bacteria, fungi, protozoa, helminths; drug induced disorders of the liver, chronic liver diseases like primary sclerosing cholangitis, alpha1-antitrypsin-deficiency, primary biliary cirrhosis, postoperative liver disorders like postoperative intrahepatic cholestasis, hepatic granulomas, vascular liver disorders associated with systemic disease, benign or malignant neoplasms of the liver, disturbance of liver metabolism in the new-born or prematurely born.

Metabolic Diseases

The human UST3 like protein 1 is highly expressed in the following metabolic disease related tissues: liver liver cirrhosis. The expression in the above mentioned tissues and in particular the differential expression between diseased tissue liver liver cirrhosis and healthy tissue liver demonstrates that the human UST3 like protein 1 or mRNA can be utilized to diagnose of metabolic diseases. Additionally the activity of the human UST3 like protein 1 can be modulated to treat metabolic diseases.

Metabolic diseases are defined as conditions which result from an abnormality in any of the chemical or biochemical transformations and their regulating systems essential to producing energy, to regenerating cellular constituents, to eliminating unneeded products arising from these processes, and to regulate and maintain homeostasis in a mammal regardless of whether acquired or the result of a genetic transformation. Depending on which metabolic pathway is involved, a single defective transformation or disturbance of its regulation may produce consequences that are narrow, involving a single body function, or broad, affecting many organs, organ-systems or the body as a whole. Diseases resulting from abnormalities related to the fine and coarse mechanisms that affect each individual transformation, its rate and direction or the availability of substrates like amino acids, fatty acids, carbohydrates, minerals, cofactors, hormones, regardless whether they are inborn or acquired, are well within the scope of the definition of a metabolic disease according to this application.

Metabolic diseases often are caused by single defects in particular biochemical pathways, defects that are due to the deficient activity of individual enzymes or molecular transporters leading to the regulation of such enzymes. Hence in a broader sense disturbances of the underlying genes, their products and their regulation lie well within the scope of this definition of a metabolic disease. For example, but not limited to, metabolic diseases may affect 1) biochemical processes and tissues ubiquitous all over the body, 2) the bone, 3) the nervous system, 4) the endocrine system, 5) the muscle including the heart, 6) the skin and nervous tissue, 7) the urogenital system, 8) the homeostasis of body systems like water and electrolytes. For example, but not limited to, metabolic diseases according to 1) comprise obesity, amyloidosis, disturbances of the amino acid metabolism like branched chain disease, hyperaminoacidemia, hyperaminoaciduria, disturbances of the metabolism of urea, hyperammonemia, mucopolysaccharidoses e.g. Maroteaux-Lamy syndrom, storage diseases like glycogen storage diseases and lipid storage diseases, glycogenosis diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or carnitine acyltransferase deficiency, disturbances of the porphyrin metabolism, porphyrias, disturbances of the purine metabolism, lysosomal diseases, metabolic diseases of nerves and nervous systems like gangliosidoses, sphingolipidoses, sulfatidoses, leucodystrophies, Lesch-Nyhan syndrome. For example, but not limited to, metabolic diseases according to 2) comprise osteoporosis, osteomalacia like osteoporosis, osteopenia, osteogenesis imperfecta, osteopetrosis, osteonecrosis, Paget's disease of bone, hypophosphatemia. For example, but not limited to, metabolic diseases according to 3) comprise cerebellar dysfunction, disturbances of brain metabolism like dementia, Alzheimer's disease, Huntington's chorea, Parkinson's disease, Pick's disease, toxic encephalopathy, demyelinating neuropathies like inflammatory neuropathy, Guillain-Barré syndrome. For example, but not limited to, metabolic diseases according to 4) comprise primary and secondary metabolic disorders associated with hormonal defects like any disorder stemming from either an hyperfunction or hypofunction of some hormone-secreting endocrine gland and any combination thereof. They comprise Sipple's syndrome, pituitary gland dysfunction and its effects on other endocrine glands, such as the thyroid, adrenals, ovaries, and testes, acromegaly, hyper- and hypothyroidism, euthyroid goiter, euthyroid sick syndrome, thyroiditis, and thyroid cancer, over- or underproduction of the adrenal steroid hormones, adrenogenital syndrome, Cushing's syndrome, Addison's disease of the adrenal cortex, Addison's pernicious anemia, primary and secondary aldosteronism, diabetes insipidus, carcinoid syndrome, disturbances caused by the dysfunction of the parathyroid glands, pancreatic islet cell dysfunction, diabetes, disturbances of the endocrine system of the female like estrogen deficiency, resistant ovary syndrome. For example, but not limited to, metabolic diseases according to 5) comprise muscle weakness, myotonia, Duchenne's and other muscular dystrophies, dystrophia myotonica of Steinert, mitochondrial myopathies like disturbances of the catabolic metabolism in the muscle, carbohydrate and lipid storage myopathies, glycogenoses, myoglobinuria, malignant hyperthermia, polymyalgia rheumatica, dermatomyositis, primary myocardial disease, cardiomyopathy. For example, but not limited to, metabolic diseases according to 6) comprise disorders of the ectoderm, neurofibromatosis, scleroderma and polyarteritis, Louis-Bar syndrome, von Hippel-Lindau disease, Sturge-Weber syndrome, tuberous sclerosis, amyloidosis, porphyria For example, but not limited to, metabolic diseases according to 7) comprise sexual dysfunction of the male and female. For example, but not limited to, metabolic diseases according to 8) comprise confused states and seizures due to inappropriate secretion of antidiuretic hormone from the pituitary gland, Liddle's syndrome, Bartter's syndrome, Fanconi's syndrome, renal electrolyte wasting, diabetes insipidus.

Hematological Disorders

The human UST3 like protein 1 is highly expressed in the following tissues of the hematological system: Jurkat (T-cells), erytlrocytes, bone marrow CD71+ cells, bone marrow CD33+ cells, bone marrow CD34+ cells, bone marrow CD15+ cells, cord blood CD71+ cells, cord blood CD34+ cells, neutrophils cord blood, neutrophils peripheral blood. The expression in the above mentioned tissues and in particular the differential expression between diseased tissue Jurkat (T-cells) and healthy tissue leukocytes (peripheral blood) demonstrates that the human UST3 like protein 1 or mRNA can be utilized to diagnose of hematological diseases. Additionally the activity of the human UST3 like protein 1 can be modulated to treat hematological disorders.

Hematological disorders comprise diseases of the blood and all its constituents as well as diseases of organs involved in the generation or degradation of the blood. They include but are not limited to 1) Anemias, 2) Myeloproliferative Disorders, 3) Hemorrhagic Disorders, 4) Leukopenia, 5) Eosinophilic Disorders, 6) Leukemias, 7) Lymphomas, 8) Plasma Cell Dyscrasias, 9) Disorders of the Spleen in the course of hematological disorders, Disorders according to 1) include, but are not limited to anemias due to defective or deficient hem synthesis, deficient erythropoiesis. Disorders according to 2) include, but are not limited to polycythemia vera, tumor-associated erythrocytosis, myelofibrosis, thrombocythemia. Disorders according to 3) include, but are not limited to vasculitis, thrombocytopenia, heparin-induced thrombocytopenia, thrombotic thrombocytopenic purpura, hemolytic-uremic syndrome, hereditary and acquired disorders of platelet function, hereditary coagulation disorders. Disorders according to 4) include, but are not limited to neutropenia, lymphocytopenia. Disorders according to 5) include, but are not limited to hypereosinophilia, idiopathic hypereosinophilic syndrome. Disorders according to 6) include, but are not limited to acute myeloic leukemia, acute lymphoblastic leukemia, chronic myelocytic leukemia, chronic lymphocytic leukemia, myelodysplastic syndrome. Disorders according to 7) include, but are not limited to Hodgkin's disease, non-Hodgkin's lymphoma, Burkitt's lymphoma, mycosis fungoides cutaneous T-cell lymphoma. Disorders according to 8) include, but are not limited to multiple myeloma, macroglobulinemia, heavy chain diseases. In extension of the preceding idiopathic thrombocytopenic purpura, iron deficiency anemia, megaloblastic anemia (vitamin B12 deficiency), aplastic anemia, thalassemia, malignant lymphoma bone marrow invasion, malignant lymphoma skin invasion, haemolytic uraemic syndrome, giant platelet disease are considered to be hematological diseases too.

Respiratory Diseases

The human UST3 like protein 1 is highly expressed in the following tissues of the respiratory system: bone marrow CD15+ cells, neutrophils cord blood, neutrophils peripheral blood, fetal lung, lung right upper lobe, lung right lower lobe, lung tumor, lung COPD. The expression in the above mentioned tissues and in particular the differential expression between diseased tissue lung tumor and healthy tissue lung, between diseased tissue lung COPD and healthy tissue lung demonstrates that the human UST3 like protein 1 or mRNA can be utilized to diagnose of respiratory diseases. Additionally the activity of the human UST3 like protein 1 can be modulated to treat those diseases.

Allergy is a complex process in which environmental antigens induce clinically adverse reactions. Asthma can be understood as an basically allergic disease of the lung and its tissues. The asthma inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction. Hypersensitivity reactions can be local or systemic and typically occur within minutes after allergen exposure in individuals who have previously been sensitized to the respective allergen. The hypersensitivity reaction of allergy develops when the allergen is recognized by IgE antibodies bound to specific transporters on the surface of effector cells, such as mast cells, basophils, or eosinophils, which causes the activation of the effector cells and the release of mediators that produce the acute signs and symptoms of the reactions. Allergic diseases include asthma, allergic rhinitis (hay fever), atopic dermatitis, and anaphylaxis.

Asthma is though to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to tissue destruction related to the disorder. Other resident cells, such as smooth muscle cells, lung epithelial cells, mucus-producing cells, and nerve cells may also be abnormal in individuals with asthma and may contribute to its pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually makes asthma a chronic and disabling disorder requiring long-term management.

Despite recent important advances in our understanding of the pathophysiology of allergies and asthma, they appear to be increasing in prevalence and severity [Cawkwell et al. (1993)]. It is estimated that 30-40% of the population suffer with atopic allergy, and 15% of children and 5% of adults in the population suffer from asthma Thus, an enormous burden is placed on our health care resources. However, both diagnosis and treatment of asthma are difficult. The severity of lung tissue inflammation is not easy to measure and the symptoms of the disease are often indistinguishable from those of respiratory infections, chronic respiratory inflammatory disorders, allergic rhinitis, or other respiratory disorders. Often, the inciting allergen cannot be determined, making removal of the causative environmental agent difficult. Current pharmacological treatments suffer their own set of disadvantages. Commonly used therapeutic agents, such as beta agonists, can act as symptom relievers to transiently improve pulmonary function, but do not affect the underlying inflammation. Agents that can reduce the underlying inflammation, such as anti-inflammatory steroids, may have major drawbacks which range from immunosuppression to bone loss. In addition, many of the present therapies, such as inhaled corticosteroids, are short-lasting, inconvenient to use, and must be used often on a regular, in some cases lifelong basis, making failure of patients to comply with the treatment a major problem and thereby reducing their effectiveness as a treatment. Because of the problems associated with conventional therapies, alternative treatment strategies have been evaluated. Glycophorin A, cyclosporin and a nonapeptide fragment of IL-2 all inhibit interleukin-2 dependent T lymphocyte proliferation; however, they are known to have many other effects. For example, cyclosporin is used as a immunosuppressant after organ transplantation. While these agents may represent alternatives to steroids in the treatment of asthmatics, they inhibit interleukin-2 dependent T lymphocyte proliferation and potentially critical immune functions associated with homeostasis. Other treatments that block the release or activity of mediators of bronchoconstriction, such as cromones or anti-leukotrienes, have recently been introduced for the treatment of mild asthma, but they are expensive and not effective in all patients and it is unclear whether they affect the chronic changes associated with asthmatic inflammation at all. What is needed in the art is the identification of a treatment that can act on pathways critical to the development of asthma and that both blocks the episodic attacks of the disorder and which dampens the hyperactive allergic immune response without immunocompromising the patient.

Chronic obstructive pulmonary (or airways) disease (COPD) is a condition defined physiologically as airflow obstruction that generally results from a mixture of emphysema and peripheral airway obstruction due to chronic bronchitis [Botstein et al. (1980)]. Emphysema is characterised by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does also occur in non-smokers.

Chronic inflammation of the airways is a key pathological feature of COPD. The inflammatory cell population comprises increased numbers of macrophages, neutrophils and CD8+ lymphocyes. Inhaled irritants such as cigarette smoke activate macrophages resident in the respiratory tract as well as epithelial cells leading to release of chemokines (e.g., interleukin-8) and other chemotactic factors which act to increase the neutrophil/monocyte trafficking from the blood into lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction and mucus hypersecretion are all potential sequelae of this inflammatory response that lead to impaired airflow and gas exchange.

Neurological Disorders

The human UST3 like protein 1 is highly expressed in the following brain tissues: brain, Alzheimer brain, cerebral cortex, Alzheimer cerebral cortex, frontal lobe, Alzheimer brain frontal lobe, occipital lobe, parietal lobe, temporal lobe, precentral gyrus, substantia nigra, cerebral meninges, hippocampus, neuroblastoma IMR32 cells, retina. The expression in brain tissues and in particular the differential expression between diseased tissue Alzheimer brain and healthy tissue brain, between diseased tissue Alzheimer cerebral cortex and healthy tissue cerebral cortex, between diseased tissue Alzheimer brain frontal lobe and healthy tissue frontal lobe demonstrates that the human UST3 like protein 1 or mRNA can be utilized to diagnose nervous system diseases. Additionally the activity of the human UST3 like protein 1 can be modulated to treat nervous system diseases.

CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoffs psychosis, within the meaning of the invention are also considered to be CNS disorders.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be CNS disorders.

Pain, within the meaning of the invention, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminai neuralgia, cranial neuralgias, and post-herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania are also CNS disorders. Visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Urological Disorders

The human UST3 like protein 1 is highly expressed in the following urological tissues: ureter. The expression in the above mentioned tissues demonstrates that the human UST3 like protein 1 or mRNA can be utilized to diagnose of urological disorders. Additionally the activity of the human UST3 like protein 1 can be modulated to treat urological disorders.

Genitourological disorders comprise benign and malign disorders of the organs constituting the genitourological system of female and male, renal diseases like acute or chronic renal failure, immunologically mediated renal diseases like renal transplant rejection, lupus nephritis, immune complex renal diseases, glomerulopathies, nephritis, toxic nephropathy, obstructive uropathies like benign prostatic hyperplasia (BPH), neurogenic bladder syndrome, urinary incontinence like urge-, stress-, or overflow incontinence, pelvic pain, and erectile dysfunction.

Cardiovascular Disorders

The human UST3 like protein 1 is highly expressed in the following cardiovascular related tissues: heart atrium (right), heart atrium (left), pulmonic valve, HUVEC cells, liver, liver tumor and liver liver ciffhosis. Expression in the above mentioned tissues demonstrates that the human UST3 like protein 1 or mRNA can be utilized to diagnose of cardiovascular diseases. Additionally the activity of the human UST3 like protein 1 can be modulated to treat cardiovascular diseases.

Heart failure is defined as a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

Cardiovascular diseases include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

Too high or too low levels of fats in the bloodstream, especially cholesterol, can cause long-term problems. The risk to develop atherosclerosis and coronary artery or carotid artery disease (and thus the risk of having a heart attack or stroke) increases with the total cholesterol level increasing. Nevertheless, extremely low cholesterol levels may not be healthy. Examples of disorders of lipid metabolism are hyperlipidemia (abnormally high levels of fats (cholesterol, triglycerides, or both) in the blood, may be caused by family history of hyperlipidemia, obesity, a high-fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type III hyperlipoproteinemia, type IV hyperlipoproteinemia, or type V hyperlipoproteinemia), hypolipoproteinemia, lipidoses (caused by abnormalities in the enzymes that metabolize fats), Gaucher's disease, Niemann-Pick disease, Fabry's disease, Wolman's disease, cerebrotendinous xanthomatosis, sitosterolemia, Refsum's disease, or Tay-Sachs disease.

Kidney disorders may lead to hyper or hypotension. Examples for kidney problems possibly leading to hypertension are renal artery stenosis, pyelonephritis, glomerulonephritis, kidney tumors, polycistic kidney disease, injury to the kidney, or radiation therapy affecting the kidney. Excessive urination may lead to hypotension.

Applications

The present invention provides for both prophylactic and therapeutic methods for gastrointestinal and liver diseases, metabolic diseases, hematological disorders, respiratory diseases, neurological disorders, urological disorders and cardiovascular diseases.

The regulatory method of the invention involves contacting a cell with an agent that modulates one or more of the activities of UST3-LIKE1. An agent that modulates activity can be an agent as described herein, such as a nucleic acid or a protein, a naturally-occurring cognate ligand of the polypeptide, a peptide, a peptidomimetic, or any small molecule. In one embodiment, the agent stimulates one or more of the biological activities of UST3-LIKE1. Examples of such stimulatory agents include the active UST3-LIKE1 and nucleic acid molecules encoding a portion of UST3-LIKE1. In another embodiment, the agent inhibits one or more of the biological activities of UST3-LIKE1. Examples of such inhibitory agents include antisense nucleic acid molecules and antibodies. These regulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by unwanted expression or activity of UST3-LIKE1 or a protein in the UST3-LIKE1 signaling pathway. In one embodiment, the method involves administering an agent like any agent identified or being identifiable by a screening assay as described herein, or combination of such agents that modulate say upregulate or downregulate the expression or activity of UST3-LIKE1 or of any protein in the UST3-LIKE1 signaling pathway. In another embodiment, the method involves administering a regulator of UST3-LIKE1 as therapy to compensate for reduced or undesirably low expression or activity of UST3-LIKE1 or a protein in the UST3-LIKE1 signalling pathway.

Stimulation of activity or expression of UST3-LIKE1 is desirable in situations in which activity or expression is abnormally low and in which increased activity is likely to have a beneficial effect. Conversely, inhibition of activity or expression of UST3-LIKE1 is desirable in situations in which activity or expression of UST3-LIKE1 is abnormally high and in which decreasing its activity is likely to have a beneficial effect.

This invention is further illustrated by the following examples which should not be construed as limiting. The contents of all references, patents and published patent applications cited throughout this application are hereby incorporated by reference.

Pharmaceutical Compositions

This invention further pertains to novel agents identified by the above-described screening assays and uses thereof for treatments as described herein.

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of UST3-LIKE1 expression or activity (and/or a regulator of the activity or expression of a protein in the UST3-LIKE1 signalling pathway) as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of UST3-LIKE1 activity or which reduce UST3-LIKE1 expression, the instructions would specify use of the pharmaceutical composition for treatment of gastrointestinal and liver diseases, metabolic diseases, hematological disorders, respiratory diseases, neurological disorders, urological disorders and cardiovascular diseases. For regulators that are agonists of UST3-LIKE1 activity or increase UST3-LIKE1 expression, the instructions would specify use of the pharmaceutical composition for treatment of gastrointestinal and liver diseases, metabolic diseases, hematological disorders, respiratory diseases, neurological disorders, urological disorders and cardiovascular diseases.

An antagonist of UST3-LIKE1 may be produced using methods which are generally known in the art. In particular, purified UST3-LIKE1 may be used to produce antibodies or to screen libraries of pharmaceutical agents to identify those which specifically bind UST3-LIKE1. Antibodies to UST3-LIKE1 may also be generated using methods that are well known in the art. Such antibodies may include, but are not limited to, polyclonal, monoclonal, chimeric, single chain antibodies, Fab fragments, and fragments produced by a Fab expression library. Neutralizing antibodies like those which inhibit dimer formation are especially preferred for therapeutic use.

In another embodiment of the invention, the polynucleotides encoding UST3-LIKE1, or any fragment or complement thereof, may be used for therapeutic purposes. In one aspect, the complement of the polynucleotide encoding UST3-LIKE1 may be used in situations in which it would be desirable to block the transcription of the mRNA. In particular, cells may be transformed with sequences complementary to polynucleotides encoding UST3-LIKE1. Thus, complementary molecules or fragments may be used to modulate UST3-LIKE1 activity, or to achieve regulation of gene function. Such technology is now well known in the art, and sense or antisense oligonucleotides or larger fragments can be designed from various locations along the coding or control regions of sequences encoding UST3-LIKE1.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding UST3-LIKE1. checklit: These techniques are described, for example, in [Scott and Smith (1990) Science 249:386-390].

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition containing UST3-LIKE1 in conjunction with a pharmaceutically acceptable carrier, for any of the therapeutic effects discussed above. Such pharmaceutical compositions may consist of UST3-LIKE1, antibodies to UST3-LIKE1, and mimetics, agonists, antagonists, or inhibitors of UST3-LIKE1. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene-diaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL.TM. (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Bio-degradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For pharmaceutical compositions which include an antagonist of UST3-LIKE1 activity, a compound which reduces expression of UST3-LIKE1, or a compound which reduces expression or activity of a protein in the UST3-LIKE1 signaling pathway or any combination thereof, the instructions for administration will specify use of the composition for gastrointestinal and liver diseases, metabolic diseases, hematological disorders, respiratory diseases, neurological disorders, urological disorders and cardiovascular diseases. For pharmaceutical compositions which include an agonist of UST3-LIKE1 activity, a compound which increases expression of UST3-LIKE1, or a compound which increases expression or activity of a protein in the UST3-LIKE1 signaling pathway or any combination thereof, the instructions for administration will specify use of the composition for gastrointestinal and liver diseases, metabolic diseases, hematological disorders, respiratory diseases, neurological disorders, urological disorders and cardiovascular diseases.

Diagnostics

In another embodiment, antibodies which specifically bind UST3-LIKE1 may be used for the diagnosis of disorders characterized by the expression of UST3-LIKE1, or in assays to monitor patients being treated with UST3-LIKE1 or agonists, antagonists, and inhibitors of UST3-LIKE1. Antibodies useful for diagnostic purposes may be prepared in the same manner as those described above for therapeutics. Diagnostic assays for UST3-LIKE1 include methods which utilize the antibody and a label to detect UST3-LIKE1 in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring UST3-LIKE1, including ELISAs, RIAs, and FACS, are known in the art and provide a basis for diagnosing altered or abnormal levels of UST3-LIKE1 expression. Normal or standard values for UST3-LIKE1 expression are established by combining body fluids or cell extracts taken from normal mammalian subjects, preferably human, with antibody to UST3-LIKE1 under conditions suitable for complex formation The amount of standard complex formation may be quantified by various methods, preferably by photometric means. Quantities of UST3-LIKE1 expressed in subject samples from biopsied tissues are compared with the standard values. Deviation between standard and subject values establishes the parameters for diagnosing disease.

In another embodiment of the invention, the polynucleotides encoding UST3-LIKE1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of UST3-LIKE1 may be correlated with disease. The diagnostic assay may be used to distinguish between absence, presence, and excess expression of UST3-LIKE1, and to monitor regulation of UST3-LIKE1 levels during therapeutic intervention.

Polynucleotide sequences encoding UST3-LIKE1 may be used for the diagnosis of a gastrointestinal and liver diseases, metabolic diseases, hematological disorders, respiratory diseases, neurological disorders, urological disorders and cardiovascular diseases disorder associated with expression of UST3-LIKE1. The polynucleotide. sequences encoding UST3-LIKE1 may be used in Southern-, Northern-, or dot-blot analysis, or other membrane-based technologies; in PCR technologies; in dipstick, pin, and ELISA assays; and in microarrays utilizing fluids or tissues from patient biopsies to detect altered UST3-LIKE1 expression. Such qualitative or quantitative methods are well known in the art.

In a particular aspect, the nucleotide sequences encoding UST3-LIKE1 may be useful in assays that detect the presence of associated disorders, particularly those mentioned above. The nucleotide sequences encoding UST3-LIKE1 may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding UST3-LIKE1 in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of gastrointestinal and liver diseases, metabolic diseases, hematological disorders, respiratory diseases, neurological disorders, urological disorders and cardiovascular diseases associated with expression of UST3-LIKE1, a normal or standard profile for expression is established. This may be accomplished by combining body fluids or cell extracts taken from normal subjects, either animal or human, with a sequence, or a fragment thereof, encoding UST3-LIKE1, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Another technique for drug screening which may be used provides for high through-put screening of compounds having suitable binding affinity to the protein of interest as described in published PCT application WO84/03564. In this method, large numbers of different small test compounds are synthesized on a solid substrate, such as plastic pins or some other surface. The test compounds are reacted with UST3-LIKE1, or fragments thereof, and washed. Bound UST3-LIKE1 is then detected by methods well known in the art. Purified UST3-LIKE1 can also be coated directly onto plates for use in the aforementioned drug screening techniques. Alternatively, non-neutralizing antibodies can be used to capture the peptide and immobilize it on a solid support.

In, another embodiment, one may use competitive drug screening assays in which neutralizing antibodies capable of binding UST3-LIKE1 specifically compete with a testcompound for binding UST3-LIKE1. In this manner, antibodies can be used to detect the presence of any peptide which shares one or more antigenic determinants with UST3-LIKE1.

Transporter are ubiquitous in the mammalian host and are responsible for many biological functions, including many pathologies. Accordingly, it is desirable to find compounds and drugs which stimmulate the activity of transporters on the one hand and which can inhibit the function of a transporter on the other hand. In particular, compounds which activate the transporters of the present invention are useful in treating various cardiovascular ailments such as caused by the lack of pulmonary blood flow or hypertension. In addition these compounds may also be used in treating various physiological disorders relating to abnormal control of fluid and electrolyte homeostasis and in diseases associated with abnormal angiotensin-induced aldosterone secretion.

Determination of a Therapeutically Effective Dose

The determination of a therapeutically effective dose is well within the capability of those skilled in the art. A therapeutically effective dose refers to that amount of active ingredient which increases or decreases UST3-LIKE1 activity relative to UST3-LIKE1 activity which occurs in the absence of the therapeutically effective dose. For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 micrograms to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

If the expression product is mRNA, the reagent is preferably an antisense oligonucleotide or a ribozyme. Polynucleotides which express antisense oligonucleotides or ribozymes can be introduced into cells by a variety of methods, as described above. Preferably, a reagent reduces expression of UST3-LIKE1 gene or the activity of UST3-LIKE1 by at least about 10, preferably about 50, more preferably about 75, 90, or 100% relative to the absence of the reagent. The effectiveness of the mechanism chosen to decrease the level of expression of UST3-LIKE1. gene or the activity of UST3-LIKE1 can be assessed using methods well known in the art, such as hybridization of nucleotide probes to UST3-LIKE1-specific mRNA, quantitative RT-PCR, immunologic detection of UST3-LIKE1, or measurement of UST3-LIKE1 activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

Nucleic acid molecules of the invention are those nucleic acid molecules which are contained in a group of nucleic acid molecules consisting of (i) nucleic acid molecules encoding a polypeptide comprising the amino acid sequence of SEQ ID NO:2, (ii) nucleic acid molecules comprising the sequence of SEQ ID NO:1, (iii) nucleic acid molecules having the sequence of SEQ ID NO:1, (iv)nucleic acid molecules the complementary strand of which hybridizes under stringent conditions to a nucleic acid molecule of (i), (ii), or (iii); and (v) nucleic acid molecules the sequence of which differs from the sequence of a nucleic acid molecule of (iii) due to the degeneracy of the genetic code, wherein the polypeptide encoded by said nucleic acid molecule has UST3-LIKE1 activity.

Polypeptides of the invention are those polypeptides which are contained in a group of polypeptides consisting of (i)polypeptides having the sequence of SEQ ID NO:2, (ii) polypeptides comprising the sequence of SEQ ID NO:2, (iii) polypeptides encoded by nucleic acid molecules of the invention and (iv) polypeptides which show at least 99%, 98%, 95%, 90%, or 80% homology with a polypeptide of (i), (ii), or (iii), wherein said purified polypeptide has UST3-LIKE1 activity.

It is an objective of the invention to provide a vector comprising the nucleic acid molecule of the invention.

Another object of the invention is a host cell containing a vector of the invention.

Another object of the invention is a method of producing a UST3-LIKE1 comprising the steps of (i) culturing a host cell of the invention under suitable conditions and (ii) recovering the UST3-LIKE1 from the culture medium.

Another object of the invention is a method for the detection of a polynucleotide encoding a UST3-LIKE1 in a sample comprising the steps of (i) hybridizing a polynucleotide of the invention to nucleic acid material of the sample, thereby forming a hybridization complex; and (ii) detecting said hybridization complex.

Another object of the invention is a method for the detection of a polynucleotide encoding a UST3-LIKE1 in a sample comprising the steps of (i) hybridizing a polynucleotide of the invention to nucleic acid material of the sample, thereby forming a hybridization complex; and (ii) detecting said hybridization complex, wherein, before hybridization, the nucleic acid material of the sample is amplified.

Another object of the invention is a method for the detection of a polynucleotide of the invention or a polypeptide of the invention comprising the steps of (i) contacting a sample with a reagent which specifically interacts with a polynucleotide of the invention or a polypeptide of the invention, and (ii) detecting said interaction.

Another object of the invention are diagnostic kits for conducting any of the methods above.

Regulators of a given protein, within the meaning of the invention, are understood as being compounds which alter either directly or indirectly the activity of the given protein either in vivo or in vitro. Alteration of the activity can be, e.g., but not limited to, by allosteric effects or by affecting the expression of the given protein.

Other objects of the invention are methods for screening for regulators of the activity of a UST3-LIKE1 comprising the steps of (i) contacting a test compound with a polypeptide of the invention, (ii) detect binding of said test compound to said polypeptide of the invention, wherein test compounds that bind under (ii) are identified as potential regulators of the UST3-LIKE1 activity.

Other objects of the invention are methods of the above, wherein the step of contacting is in or at the surface of a cell.

Other objects of the invention are methods of the above, wherein the step of contacting is in or at the surface of a cell wherein the cell is in vitro.

Other objects of the invention are methods of the above, wherein the step of contacting is in a cell-free system.

Other objects of the invention are methods of the above, wherein the polypeptide of the invention is coupled to a detectable label.

Other objects of the invention are methods of the above, wherein the compound is coupled to a detectable label.

Other objects of the invention are methods of the above, wherein the test compound displaces a ligand which is first bound to the polypeptide.

Other objects of the invention are methods of the above, wherein the polypeptide of the invention is attached to a solid support.

Other objects of the invention are methods of the above, wherein the compound is attached a solid support.

Another object of the invention is a method of screening for regulators of the activity of a UST3-LIKE1 comprising the steps of (i) measuring the activity of a polypeptide of the invention at a certain concentration of a test compound or in the absence of said test compound, (ii) measuring the activity of said polypeptide at a different concentrations of said test compound, wherein said test compound is identified as a regulator of the activity of a UST3-LIKE1 when there is a significant difference between the activities measured in (i) and (ii).

Another object of the invention is a method of screening for regulators of the activity of a UST3-LIKE1 comprising the steps of (i) measuring the activity of a polypeptide of the invention at a certain concentration of a test compound, (ii) measuring the activity of a polypeptide of the invention at the presence of a compound known to be a regulator of UST3-LIKE1.

Another object of the invention is a method of screening for regulators of the activity of a UST3-LIKE1 comprising the aforementioned methods, wherein the activities are measured in a cell.

Another object of the invention is a method of screening for regulators of the activity of a UST3-LIKE1 comprising the aforementioned methods, wherein the cell is in vitro.

Another object of the invention is a method of screening for regulators of the activity of a UST3-LIKE1 comprising the aforementioned methods, wherein the activities are measured in a cell-free system.

Another object of the invention is a method of screening for regulators of UST3-LIKE1 comprising the steps of (i) contacting a test compound with a nucleic acid molecule of the invention, (ii) detect binding of said test compound to said nucleic acid molecule, wherein said test compound is identified as a potential regulator of UST3-LIKE1 when it binds to said nucleic acid molecule.

Another object of the invention is a method of screening for regulators of UST3-LIKE1 comprising the steps of (i) contacting a test compound with a nucleic acid molecule of the invention, wherein the nucleic acid molecule is an RNA (ii) detect binding of said test compound to said RNA molecule, wherein said test compound is identified as a potential regulator of UST3-LIKE1 when it binds to said RNA molecule.

Another object of the invention is a method of screening for regulators of UST3-LIKE1 comprising the steps of contacting a test compound with a nucleic acid molecule of the invention, detect binding of said test compound to said nucleic acid molecule, wherein said test compound is identified as a potential regulator of UST3-LIKE1 when it binds to said nucleic acid molecule, wherein the contacting step is (i) in or at the surface of a cell or (ii) in a cell-free system or wherein (iii) the polypeptide or nucleic acid molecule is coupled to a detectable label or wherein (iv) the test compound is coupled to a detectable label.

Another object of the invention is a method of regulating the activity of a UST3-LIKE1 wherein UST3-LIKE1 is contacted with a regulator of UST3-LIKE1.

Another object of the invention is a method of diagnosing a UST3-LIKE1 related disease in a diseased mammal comprising the steps of (i) measuring the amount of a nucleic acid molecule of the invention in a sample taken from said diseased mammal, (ii) comparing the result of (i) to the amount of said nucleic acid molecule in one or several healthy mammals, wherein a UST3-LIKE1 related disease is diagnosed in the diseased mammal when the amount of said nucleic acid molecule in the diseased mammal is significantly different from the amount of said nucleic acid molecule in the healthy mammal/mammals.

Other objects of the invention are pharmaceutical compositions comprising (i) a nucleic acid molecule of the invention, (ii) a vector of the invention, or (iii) a polypeptide of the invention.

Another object of the invention are pharmaceutical compositions comprising a regulator of the invention.

Another object of the invention are pharmaceutical compositions comprising a regulator identified by methods of the invention for the treatment of hematological disorders, peripheral and central nervous system disorders, COPD, asthma, genito-urological disorders, metabolic diseases, pancreas disorders or heart disorders in a mammal.

Another object of the invention regards the use of regulators of a UST3-LIKE1 as identified by any of the aforementioned methods for the preparation of pharmaceutical compositions useful for the treatment of hematological disorders, peripheral and central nervous system disorders, COPD, asthma, genito-urological disorders, metabolic diseases, pancreas disorders or heart disorders in a mammal.

Another object of the invention are methods for the preparation of pharmaceutical compositions useful for the treatment of hematological disorders, peripheral and central nervous system disorders, COPD, asthma, genito-urological disorders, metabolic diseases, pancreas disorders or heart disorders in a mammal comprising the steps of (i) identifying a regulator of UST3-LIKE1 by any of the aforementioned methods, (ii) determining of whether said regulator ameliorates the symptoms of gastrointestinal and liver diseases, metabolic diseases, hematological disorders, respiratory diseases, neurological disorders, urological disorders and cardiovascular diseases in a mammal, (iii) combining of said regulator with an acceptable pharmaceutical carrier.

Another object of the invention is the use of a regulator of UST3-LIKE1 as identified by any of the aforementioned methods for (i) the treatment of gastrointestinal and liver diseases, metabolic diseases, hematological disorders, respiratory diseases, neurological disorders, urological disorders and cardiovascular diseases in a mammal, or (ii) use of a regulator of UST3-LIKE1 for the regulation of UST3-LIKE1 activity in a mammal having a gastrointestinal and liver diseases, metabolic diseases, hematological disorders, respiratory diseases, neurological disorders, urological disorders and cardiovascular diseases.

Another object of the invention is the use of any of the aforementioned pharmaceutical compositions wherein the regulator of UST3-LIKE1 is either a small molecule, an RNA molecule, or an antisense oligonucleotide, or a polypeptide, an antibody, or a ribozyme. Small molecules, within the meaning of the invention, are organic molecules of a molecular weight of less than one thousand five hundred grams per mol.

The examples below are provided to illustrate the subject invention. These examples are provided by way of illustration and are not included for the purpose of limiting the invention.

EXAMPLES

Example 1

Search for Homologous Sequences in Public Sequence Data Bases

The degree of homology can readily be calculated by known methods. Preferred methods to determine homology are designed to give the largest match between the sequences tested. Methods to determine homology are codified in publicly available computer programs such as BestFit, BLASTP, BLASIN, and FASTA. The BLAST programs are publicly available from NCBI and other sources in the internet.

For UST3-LIKE1 the following hits to known sequences were identified by using the BLAST algorithm [Altschul et al. (1997)] and the following set of parameters: matrix=BLOSUM62 and low complexity filter. The following databases were searched: NCBI (non-redundant database) and DERWENT patent database (Geneseq). The following hits were found:

>ref |NM_080866.1| *Homo sapiens* solute carrier family 22 (organic anion/cation transporter), member 9 (SLC22A9), mRNA, Length=2192, Score=1277 bits (664), Expect=0.0, Identities=1127/1351 (83%), Gaps=6/1351 (0%)

>dbj |AK074246.1| *Homo sapiens* cDNA FLJ23666 fis, clone HEP04439, Length=2192, Score=1277 bits (664), Expect=0.0, Identities=1127/1351 (83%), Gaps=6/1351 (0%)

>emb |AJ295270.1|HSA295270 Homo sapiens mRNA for putative integral membrane transport protein (UST3H gene), Length=1898, Score=1240 bits (645), Expect=0.0, Identities=1018/1202 (84%), Gaps=3/1202 (0%)

>dbj |BD161113.1| Polypeptide having transporter activity and gene encoding the peptide, Length=1846, Score=1235 bits (642), Expect=0.0, Identities=1017/1202 (84%), Gaps=3/1202 (0%)

>dbj |AB062418.1| *Homo sapiens* ust3 mRNA for hUST3, complete cds, Length=1846, Score=1235 bits (642), Expect=0.0, Identities=1017/1202 (84%), Gaps=3/1202 (0%)

>emb |AX179749.1| Sequence 37 from Patent WO0146258, Length=1986, Score=1200 bits (624), Expect=0.0, Identities=1011/1202 (84%), Gaps=3/1202 (0%)

>emb |AX074149.1| Sequence 5 from Patent WO0104283, Length=1977, Score=1194 bits (621), Expect=0.0, Identities=1010/1202 (84%), Gaps=3/1202 (0%)

>dbj |AK091990.1| *Homo sapiens* cDNA FLJ34671 fis, clone LIVER2001099, moderately similar to Rattus norvegicus mRNA for putative integral membrane transport protein, Length=2324, Score=1075 bits (559), Expect=0.0, Identities=565/568 (99%)

>dbj |AP003420.2| *Homo sapiens* genomic DNA, chromosome 11q, clone:RP11-614K12, complete sequence, Length=160945, Score=890 bits (463), Expect=0.0, Identities=463/463 (100%)

Example 2

Expression Profiling

Total cellular RNA was isolated from cells by one of two standard methods: 1) guanidine isothiocyanate/Cesium chloride density gradient centrifugation [Kellogg et al. (1990)]; or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination.

For relative quantitation of the mRNA distribution of the human UST3 like protein 1, total RNA from each cell or tissue source was first reverse transcribed. 85 μg of total RNA was reverse transcribed using 1 μmole random hexamer primers, 0.5 mM each of dATP, dCTP, dGTP and dTTP (Qiagen, Hilden, Germany), 3000 U RnaseQut (Invitrogen, Groningen, Netherlands) in a final volume of 680 μl. The first strand synthesis buffer and Omniscript reverse transcriptase (2 u/μl) were from (Qiagen, Hilden, Germany). The reaction was incubated at 37° C. for 90 minutes and cooled on ice. The volume was adjusted to 6800 μl with water, yielding a final concentration of 12.5 ng/μl of starting RNA.

For relative quantitation of the distribution of the human UST3 like protein 1 mRNA in cells and tissues the Applied Biosystems 7900HT Sequence Detection system was used according to the manufacturer's specifications and protocols. PCR reactions were set up to quantitate the human UST3 like protein 1 and the housekeeping genes HPRT (hypoxanthine phosphoribosyltransferase), GAPDH (glyceraldehyde-3-phosphate dehydrogenase), β-actin, and others. Forward and reverse primers and probes for the human UST3 like protein 1 were designed using the Perkin Elmer ABI Primer Express™ software and were synthesized by TibMolBiol (Berlin, Germany). The human UST3 like protein 1 forward primer sequence was: Primer1 (SE Q ID NO: 3). The human UST3 like protein 1 reverse primer sequence was Primer2 (SEQ ID NO: 5). Probe1 (SEQ ID NO: 4), labelled with FAM (carboxyfluorescein succinimidyl ester) as the reporter dye and TAMRA (carboxytetramethylrhodamine) as the quencher, is used as a probe for the human UST3 like protein 1. The following reagents were prepared in a total of 25 μl : 1× TaqMan buffer A, 5.5 MM $MgCl_2$, 200 nM of dATP, dCTP, dGTP, and dUTP, 0.025 U/μl AmpliTaq Gold™, 0.01 U/μl AmpErase and Probe1 (SEQ ID NO: 4), human UST3 like protein 1 forward and reverse primers each at 200 nM, 200 nM, human UST3 like protein 1 FAM/TAMRA-labelled probe, and 5 μl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Corrected CT Values

The CT (threshold cycle) value is calculated as described in the "Quantitative determination of nucleic acids" section. The CF-value (factor for threshold cycle correction) is calculated as follows:

1. PCR reactions were set up to quantitate the housekeeping genes (HKG) for each cDNA sample.
2. $CT_{HKG}$-values (threshold cycle for housekeeping gene) were calculated as described in the "Quantitative determination of nucleic acids" section.
3. $CT_{HKG}$-mean values (CT mean value of all HKG tested on one cDNAs) of all HKG for each cDNA are calculated (n=number of HKG):

$CT_{HKG-n}$-mean value=$(CT_{HKG1}$-value+$CT_{HKG2}$-value+ . . . +$CT_{HKG-n}$-value$)/n$ 4. $CT_{pannel}$ mean value (CT mean value of all HKG in all tested cDNAs)=$(CT_{HKG1}$-mean value+$CT_{HKG2}$-mean value+ . . . +$CT_{HKG-y}$-mean value)/y (y=number of cDNAs)
5. $CF_{cDNA-n}$ (correction factor for cDNA n)=$CT_{pannel}$-mean value−$CT_{HKG-n}$-mean value
6. $CT_{cDNA-n}$ (CT value of the tested gene for the cDNA n)+$CF_{cDNA-n}$ (correction factor for cDNA n)= $CT_{cor-cDNA-n}$ (corrected CT value for a gene on cDNA n)

Calculation of Relative Expression

Definition: highest $CT_{cor-cDNA-n}\neq40$ is defined as $CT_{cor-cDNA}$ [high]Relative Expression= $2^{(CTcor-cDNA[high]-CTcor-cDNA-n)}$ Human Tissues fetal heart, heart, pericardium, heart atrium (right), heart atrium (left), heart ventricle (left), heart ventricle (right), heart apex, Purkinje fibers, interventricular septum, fetal aorta, aorta, artery, coronary artery, pulmonary artery, carotid artery, mesenteric artery, vein, pulmonic valve, coronary artery smooth muscle primary cells, HUVEC cells, skin, adrenal gland, thyroid, thyroid tumor, pancreas, pancreas liver cirrhosis, esophagus, esophagus tumor, stomach, stomach tumor, colon, colon tumor, small intestine, ileum, ileum tumor, ileum chronic inflammation, rectum, salivary gland, fetal liver, liver, liver liver cirrhosis, liver tumor, HEP G2 cells, leukocytes (peripheral blood), Jurkat (T-cells), bone marrow, erythrocytes, lymphnode, thymus, thrombocytes, bone marrow stromal cells, bone marrow CD71+ cells, bone marrow CD33+ cells, bone marrow CD34+ cells, bone marrow CD15+ cells, cord blood CD71+ cells, cord blood CD34+ cells, neutrophils cord blood, neutrophils peripheral blood, spleen, spleen liver cirrhosis, skeletal muscle, adipose, fetal brain, brain, Alzheimer brain, cerebellum, cerebellum (right), cerebellum (left), cerebral cortex, Alzheimer cerebral cortex, frontal lobe, Alzheimer brain frontal lobe, occipital lobe, parietal lobe, temporal lobe, precentral gyrus, postcentral gyrus, tonsilla cerebelli, vermis cerebelli, pons, substantia nigra, cerebral meninges, cerebral peduncles, corpus callosum, hippocampus, thalamus, dorsal root ganglia, spinal cord, neuro-blastoma SK-N-MC cells, neuroblastoma SH-SY5Y cells, neuroblastoma IMR32 cells, glial tumor H4 cells, glial tumor H4 cells+APP, HEK CNS, HEK CNS+APP, retina, fetal lung, fetal lung fibroblast IMR-90 cells, fetal lung fibroblast MRC-5 cells, lung, lung right upper lobe, lung right mid lobe, lung right lower lobe, lung lupus disease, lung tumor, lung COPD, trachea, cervix, testis, HeLa cells (cervix tumor), placenta, uterus, uterus tumor, ovary, ovary tumor, breast, breast tumor, MDA MB 231 cells (breast tumor), mammary gland, prostate, prostate BPH, bladder, ureter, penis, corpus cavernosum, fetal kidney, kidney, kidney tumor, HEK 293 cells Expression Profile The results of the the mRNA-quantification (expression profiling) is shown in Table 1.

TABLE 1

Relative expression of UST3-LIKE1 in various human tissues.

| Tissue | Relative Expression |
| --- | --- |
| fetal heart | 9 |
| heart | 28 |
| pericardium | 52 |
| heart atrium (right) | 162 |
| heart atrium (left) | 155 |
| heart ventricle (left) | 43 |
| heart ventricle (right) | 2 |
| heart apex | 1 |
| Purkinje fibers | 25 |
| interventricular septum | 31 |
| fetal aorta | 4 |
| aorta | 1 |
| artery | 15 |
| coronary artery | 82 |
| pulmonary artery | 10 |
| carotid artery | 1 |
| mesenteric artery | 1 |
| vein | 27 |
| pulmonic valve | 904 |
| coronary artery smooth muscle | 49 |
| HUVEC cells | 64 |
| skin | 37 |
| adrenal gland | 9 |
| thyroid | 1 |
| thyroid tumor | 4 |
| pancreas | 8 |
| pancreas liver cirrhosis | 14 |
| esophagus | 34 |
| esophagus tumor | 572 |

TABLE 1-continued

Relative expression of UST3-LIKE1 in various human tissues.

| Tissue | Relative Expression |
|---|---|
| stomach | 22 |
| stomach tumor | 239 |
| colon | 1 |
| colon tumor | 42 |
| small intestine | 3 |
| ileum | 111 |
| ileum tumor | 1585 |
| ileum chronic inflammation | 24 |
| rectum | 220 |
| salivary gland | 180 |
| fetal liver | 15393 |
| liver | 25532 |
| liver liver cirrhosis | 491 |
| liver tumor | 25355 |
| HEP G2 cells | 2978 |
| leukocytes (peripheral blood) | 5 |
| Jurkat (T-cells) | 380 |
| bone marrow | 1 |
| erythrocytes | 211 |
| lymphnode | 67 |
| thymus | 7 |
| thrombocytes | 163 |
| bone marrow stromal cells | 42 |
| bone marrow CD71+ cells | 399 |
| bone marrow CD33+ cells | 910 |
| bone marrow CD34+ cells | 622 |
| bone marrow CD15+ cells | 843 |
| cord blood CD71+ cells | 635 |
| cord blood CD34+ cells | 1082 |
| neutrophils cord blood | 1243 |
| neutrophils peripheral blood | 2798 |
| spleen | 32 |
| spleen liver cirrhosis | 1 |
| skeletal muscle | 22 |
| adipose | 107 |
| fetal brain | 50 |
| brain | 333 |
| Alzheimer brain | 962 |
| cerebellum | 2 |
| cerebellum (right) | 771 |
| cerebellum (left) | 481 |
| cerebral cortex | 4804 |
| Alzheimer cerebral cortex | 1218 |
| frontal lobe | 5634 |
| Alzheimer brain frontal lobe | 5518 |
| occipital lobe | 4182 |
| parietal lobe | 1992 |
| temporal lobe | 6841 |
| precentral gyrus | 3214 |
| postcentral gyrus | 122 |
| tonsilla cerebelli | 180 |
| vermis cerebelli | 331 |
| pons | 228 |
| substantia nigra | 27554 |
| cerebral meninges | 1252 |
| cerebral peduncles | 55 |
| corpus callosum | 580 |
| hippocampus | 4939 |
| thalamus | 294 |
| dorsal root ganglia | 126 |
| spinal cord | 8 |
| neuroblastoma SK-N-MC cells | 564 |
| neuroblastoma SH-SY5Y cells | 261 |
| Neuroblastoma IMR32 cells | 1585 |
| glial tumor H4 cells | 215 |
| glial tumor H4 cells + APP | 300 |
| retina | 4270 |
| fetal lung | 239 |
| fetal lung fibroblast IMR-90 | 41 |
| fetal lung fibroblast MRC-5 | 1 |
| lung | 9 |
| lung right upper lobe | 111 |
| lung right mid lobe | 80 |
| lung right lower lobe | 201 |
| lung lupus disease | 1 |
| lung tumor | 137 |
| lung COPD | 2 |
| trachea | 46 |
| cervix | 16 |
| testis | 36 |
| HeLa cells (cervix tumor) | 1 |
| placenta | 10 |
| uterus | 27 |
| uterus tumor | 296 |
| ovary | 1 |
| ovary tumor | 685 |
| breast | 2257 |
| breast tumor | 135 |
| MDA MB 231 cells (breast | 45 |
| mammary gland | 36 |
| prostate | 34 |
| prostate BPH | 2 |
| bladder | 3 |
| ureter | 3281 |
| penis | 600 |
| corpus cavernosum | 84 |
| fetal kidney | 639 |
| Kidney | 19 |
| Kidney tumor | 214 |
| HEK 293 cells | 124 |

Example 3

Antisense Analysis

Knowledge of the correct, complete cDNA sequence coding for UST3-LIKE1 enables its use as a tool for antisense technology in the investigation of gene function. Oligonucleotides, cDNA or genomic fragments comprising the antisense strand of a polynucleotide coding for UST3-LIKE1 are used either in vitro or in vivo to inhibit translation of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to transacting regulatory genes.

Example 4

Expression of UST3-LIKE1

Expression of UST3-LIKE1 is accomplished by subcloning the cDNAs into appropriate expression vectors and transfecting the vectors into expression hosts such as, e.g., *E. coli*. In a particular case, the vector is engineered such that it contains a promoter for β-galactosidase, upstream of the cloning site, followed by sequence containing the amino-terminal Methionine and the subsequent seven residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with Isopropyl-β-D-thiogalactopyranoside (IPTG) using standard methods produces a fusion protein corresponding to the first seven residues of β-galactosidase, about 15 residues of "linker", and the peptide encoded within the cDNA. Since cDNA clone inserts are generated by an essentially random process, there is probability of 33% that the included cDNA will lie in the correct reading frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The UST3-LIKE1 cDNA is shuttled into other vectors known to be useful for expression of proteins in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells., insect cells such as Sf9 cells, yeast cells such as *Saccharomyces cerevisiae* and bacterial cells such as *E. coli*. For each of these cell systems, a useful expression vector also includes an origin of replication to allow propagation in bacteria, and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced UST3-LIKE1 are recovered from the conditioned medium and analyzed using chromatographic methods known in the art. For example, UST3-LIKE1 can be cloned into the expression vector pcDNA3, as exemplified herein. This product can be used to transform, for example, HEK293 or COS by methodology standard in the art. Specifically, for example, using Lipofectamine (Gibco BRL catolog no. 18324-020) mediated gene transfer.

Example 5

Isolation of Recombinant UST3-LIKE1

UST3-LIKE1 is expressed as a chimeric protein with one or more additional polypeptide domains added to facilitate protein purification. Such purification facilitating domains include, but are not limited to, metal chelating peptides such as histidine-tryptophan modules that allow purification on immobilized metals [Appa Rao (1997)] and the domain utilized in the FLAGS extension/affinity purification system (Immunex Corp., Seattle, Wash.). The inclusion of a cleavable linker sequence such as Factor Xa or enterokinase (Invitrogen, Groningen, The Netherlands) between the purification domain and the UST3-LIKE1 sequence is useful to facilitate expression of UST3-LIKE1.

Example 6

Production of UST3-LIKE1 Specific Antibodies

Two approaches are utilized to raise antibodies to UST3-LIKE1, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 μg are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate UST3-LIKE1 domain, as deduced from translation of the cDNA, is analyzed to determine regions of high antigenicity. Oligopeptides comprising appropriate hydrophilic regions are synthesized and used in suitable immunization protocols to raise antibodies. The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis, Mo.) by reaction with M-maleimidobenzoyl-N-hydroxysuccinimide ester, MBS. If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled UST3-LIKE1 to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable antispecies 1 g) antibodies at 10 mg/ml. The coated wells are blocked with 1% bovine serum albumin, (BSA), washed and incubated with supernatants from hybridomas. After washing the wells are incubated with labeled UST3-LIKE1 at 1 mg/ml. Supernatants with specific antibodies bind more labeled UST3-LIKE1 than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8$ $M^{-1}$, preferably $10^9$ to $10^{10}$ $M^{-1}$ or stronger, are typically made by standard procedures.

Example 7

Diagnostic Test Using UST3-LIKE1 Specific Antibodies

Particular UST3-LIKE1 antibodies are useful for investigating signal transduction and the diagnosis of infectious or hereditary conditions which are characterized by differences in the amount or distribution of UST3-LIKE1 or downstream products of an active signaling cascade.

Diagnostic tests for UST3-LIKE1 include methods utilizing antibody and a label to detect UST3-LIKE1 in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like.

A variety of protocols for measuring soluble or membrane-bound UST3-LIKE1, using either polyclonal or monoclonal antibodies specific for the protein, are known in the art. Examples include enzyme-linked immunosorbent assay (ELISA), radio-immunoassay (RIA) and fluorescent activated cell sorting (FACS). A two-site monoclonal-based immunoassay utilizing monoclonal antibodies reactive to two non-interfering epitopes on UST3-LIKE1 is preferred, but a competitive binding assay may be employed.

Example 8

Purification of Native UST3-LIKE1 Using Specific Antibodies

Native or recombinant UST3-LIKE1 is purified by immunoaffinity chromatography using antibodies specific for UST3-LIKE1. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of UST3-LIKE1 by preparing a fraction from cells containing UST3-LIKE1 in a soluble form. This preparation is derived by solubilization of whole cells or of a subcellular fraction obtained via differential centrifugation (with or without addition of detergent) or by other methods well known in the art. Alternatively, soluble UST3-LIKE1 containing a signal sequence is secreted in useful quantity into the medium in which the cells are grown.

A soluble UST3-LIKE1-containing preparation is passed over the immunoaffinity column, and the column is washed under conditions that allow the preferential absorbance of UST3-LIKE1 (e.g., high ionic strength buffers in the presence of detergent). Then, the column is eluted under conditions that disrupt antibody/protein binding (e.g., a buffer of pH 2-3 or a high concentration of a chaotrope such as urea or thiocyanate ion), and UST3-LIKE1 is collected.

Example 9

Drug Screening

Test compounds can be screened for the ability to bind to OAT-like polypeptides or polynucleotides or to affect OAT-like activity or OAT-like gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 microliter. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614-18 (1994). The cells are placed under agarbse in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7-10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57-63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Example 10

Rational Drug Design

The goal of rational drug design is to produce structural analogs of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design include molecules which have improved activity or stability or which act as inhibitors, agonists, or antagonists of native peptides.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original transporter. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the UST3-LIKE1 amino acid sequence provided herein provides guidance to those employing computer modeling techniques in place of or in addition to x-ray crystallography.

Example 11

Use and Administration of Antibodies, Inhibitors or Antagonists

Antibodies, inhibitors, or antagonists of UST3-LIKE1 or other treatments and compounds that are limiters of signal transduction (LSTs), provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, its half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to $10^5$ μg, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger UST3-LIKE1 activity are treatable with LSTs. These conditions or diseases are specifically diagnosed by the tests discussed above, and such testing should be performed in suspected cases of viral, bacterial or fungal infections, allergic responses, mechanical injury associated with trauma, hereditary diseases, lymphoma or carcinoma, or other conditions which activate the genes of lymphoid or neuronal tissues.

Example 12

Production of Non-human Transgenic Animals

Animal model systems which elucidate the physiological and behavioral roles of the UST3-LIKE1 transporter are produced by creating nonhuman transgenic animals in which the activity of the UST3-LIKE1 transporter is either increased or decreased, or the amino acid sequence of the expressed UST3-LIKE1 transporter is altered, by a variety of techniques. Examples of these techniques include, but are not limited to: 1) Insertion of normal or mutant versions of DNA encoding a UST3-LIKE1 transporter, by microinjection, electroporation, retroviral transfection or other means well known to those skilled in the art, into appropriately fertilized embryos in order to produce a transgenic animal or 2) homologous recombination of mutant or normal, human or animal versions of these genes with the native gene locus in transgenic animals to alter the regulation of expression or the structure of these UST3-LIKE1 transporter sequences. The technique of homologous recombination is well known in the art. It replaces the native gene with the inserted gene and hence is useful for producing an animal that cannot express native UST3-LIKE1 transporters but does express, for example, an inserted mutant UST3-LIKE1 transporter, which has replaced the native UST3-LIKE1 transporter in the animal's genome by recombination, resulting in underexpression of the transporter. Microinjection adds genes to the genome, but does not remove them, and the technique is useful for producing an animal which expresses its own and added UST3-LIKE1 transporter, resulting in overexpression of the UST3-LIKE1 transporter.

One means available for producing a transgenic animal, with a mouse as an example, is as follows: Female mice are mated, and the resulting fertilized eggs are dissected out of their oviducts. The eggs are stored in an appropriate medium such as cesiumchloride M2 medium. DNA or cDNA encoding UST3-LIKE1 is purified from a vector by methods well known to the one skilled in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse which is a mouse stimulated by the appropriate hormones in order to maintain false pregnancy, where it proceeds to the uterus, implants, and develops to term. As noted above, microinjection is not the only method for inserting DNA into the egg but is used here only for exemplary purposes.

Example 13

Binding Assay

For binding assays, the test compound is preferably a small molecule which binds to a OAT-like polypeptide, thereby reducing the normal biological activity of the OAT-like polypeptide. Examples of such small molecules include, but are not limited to, small peptides or peptide-like molecules. In binding assays, either the test compound or the OAT-like polypeptide can comprise a detectable label, such as a fluorescent, radioisotopic, chemiluminescent, or enzymatic label, such as horseradish peroxidase, alkaline phosphatase, or luciferase. Detection of a test compound which is bound to the OAT-like polypeptide can then be accomplished, for example, by direct counting of radioemmission, by scintillation counting, or by determining conversion of an appropriate substrate to a detectable product.

Alternatively, binding of a test compound to a OAT-like polypeptide can be determined without labeling either of the interactants. For example, a microphysiometer can be used to detect binding of a test compound with a OAT-like polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a OAT-like polypeptide (McConnell et al., *Science* 257, 1906-1912, 1992).

Determining the ability of a test compound to bind to a OAT-like polypeptide also can be accomplished using a technology such as real-time Bimolecular Interaction Analysis (BIA) (Sjolander & Urbaniczky, *Anal. Chem.* 63, 2338-2345, 1991, and Szabo et al., *Curr. Opin. Struct. Biol.* 5, 699-705, 1995). BIA is a technology for studying biospecific interactions in real time, without labeling any of the interactants (e.g, BIAcore™). Changes in the optical phenomenon surface plasmon resonance (SPR) can be used as an indication of real-time reactions between biological molecules.

In yet another aspect of the invention, a OAT-like polypeptide can be used as a "bait protein" in a two-hybrid assay or three-hybrid assay (see, e.g., U.S. Pat. No. 5,283,317; Zervos et al., *Cell* 72, 223-232, 1993; Madura et al., *J. Biol. Chem.* 268, 12046-12054, 1993; Bartel et al., *Biotechniques* 14, 920-924, 1993; Iwabuchi et al., *Oncogene* 8, 1693-1696, 1993; and Brent WO94/10300), to identify other proteins which bind to or interact with the OAT-like polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a OAT-like polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the OAT-like polypeptide.

It may be desirable to immobilize either the OAT-like polypeptide (or polynucleotide) or the test compound to facilitate separation of bound from unbound forms of one or both of the interactants, as well as to accommodate automation of the assay. Thus, either the OAT-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the OAT-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a OAT-like polypeptide (or polynucleotide) can be accomplished in any vessel suitable for containing the reactants. Examples of such vessels include microtiter plates, test tubes, and microcentrifuge tubes.

In one embodiment, the OAT-like polypeptide is a fusion protein comprising a domain that allows the OAT-like polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed OAT-like polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a OAT-like polypeptide (or polynucleotide) or a test compound can be immobilized utilizing conjugation of biotin and streptavidin. Biotinylated OAT-like polypeptides (or polynucleotides) or test compounds can be prepared from biotin-NHS(N-hydroxy-succinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a OAT-like polypeptide, polynucleotide, or a test compound, but which do not interfere with a desired binding site, such as the active site of the OAT-like polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using anti-bodies which specifically bind to the OAT-like polypeptide or test compound, enzyme-linked assays which rely on detecting an activity of the OAT-like polypeptide, and SDS gel electrophoresis under non-reducing conditions.

Screening for test compounds which bind to a OAT-like polypeptide or polynucleotide also can be carried out in an intact cell. Any cell which comprises a OAT-like polypeptide or polynucleotide can be used in a cell-based assay system. A OAT-like polynucleotide can be naturally occurring in the cell or can be introduced using techniques such as those described above. Binding of the test compound to a OAT-like polypeptide or polynucleotide is determined as described above.

Purified OAT-like polypeptides comprising a glutathione-S-transferase protein and absorbed onto glutathione-derivatized wells of 96-well microtiter plates are contacted with test compounds from a small molecule library at pH 7.0 in a physiological buffer solution. OAT-like polypeptides comprise an amino acid sequence shown in any one or more of SEQ ID NO:6 to 10. The test compounds comprise a fluorescent tag. The samples are incubated for 5 minutes to one hour. Control samples are incubated in the absence of a test compound.

The buffer solution containing the test compounds is washed from the wells. Binding of a test compound to a OAT-like polypeptide is detected by fluorescence measurements of the contents of the wells. A test compound which increases the fluorescence in a well by at least 15% relative to fluorescence of a well in which a test compound is not incubated is identified as a compound which binds to an ADO-ribosylation factor-related polypeptide.

Example 14

Functional Activity

Functional assays can be carried out as described in the specific examples, after contacting either a purified OAT-like polypeptide or an intact cell with a test compound. A test compound which decreases a functional activity of a human OAT-like polypeptide by at least about 10, preferably about 50, more preferably about 75, 90, or 100% is identified as a potential agent for decreasing OAT-like protein activity. A test compound which increases a functional activity by at least about 10, preferably about 50, more preferably about 75, 90, or 100% is identified as a potential agent for increasing OAT-like protein activity.

Example 15

Effect of Test Compound on Anoinic Transport

Transport of $^3$H-labeled substrate in the presence or absence of a test compound can be measured as described in Hsiang et al. (1999, supra). Briefly, 293c18 cells are transfected with human OATP2-like expression constructs using LipofectAMINE Plus (Life Technologies, Inc.) according to the manufacturer's instructions. The medium is removed, and the cells are washed once in serum-free DMEM. $^3$H-labeled substrate, either alone or in the presence of a test compound, is added in the same medium and incubated at room temperature for 5-10 minutes. The cells are quickly washed once with ice-cold DMEM containing 5% bovine serum albumin, then washed three times with ice-cold DMEM. Cells are lysed in 0.1 N NaOH. Radiolabel incorporation is determined by liquid scintillation counting.

REFERENCES

U.S. Pat. No. 4,522,811
U.S. Pat. No. 4,683,195
U.S. Pat. No. 4,800,195
U.S. Pat. No. 4,965,188
U.S. Pat. No. 5,223,409
U.S. Pat. No. 5,283,317
U.S. Pat. No. 5,403,484
U.S. Pat. No. 5,565,332
U.S. Pat. No. 5,571,698
U.S. Pat. No. 5,641,673
WO 84/03564
WO 92/01810
WO 93/03151
WO 94/13804
WO 01/04283
WO 01/04297
WO 01/46258
Agrawal et al., *Trends Biotechnol.* 10, 152-158, 1992
Altschul S F, Madden T L, Schaffer A A, Zhang J, Zhang Z, Miller W, Lipman D J; Nucleic Acids Res Sep. 1, 1997; 25(17): 3389-402
Appa Rao K B, Garg L C, Panda A K, Totey S M; Protein Expr Purif 1997 November; 11(2): 201-8
Barnes, P. J. Mechanisms in COPD. Differences from asthma. Chest 2000, 117:10S14S
Bartel et al., *BioTechniques* 14, 920-924, 1993
Becker-Andre, M., Meth. Mol. Cell Biol. 2:189-201 (1991)
Botstein D, W. R., Skolnick M, Davis R W., Am J Hum Genet. 32: 314-31, 1980.
Burton, *Proc. Natl. Acad Sci.* 88, 11120-23, 1991
Carrell et al. (1994) Angew. Chem. Int. Ed. Engl. 33:2059
Caruthers et al., *Nucl. Acids Res. Symp. Ser.* 215-223, 1980
Cawkwell L, B. S., Lewis F A, Dixon M F, Taylor G R, Quirke P, Br J Cancer. 67: 1262-7, 1993.
Cech, *Science* 236, 1532-1539; 1987
Cech, *Ann. Rev. Biochem.* 59, 543-568; 1990
Cech, *Curr. Opin. Struct. Biol.* 2, 605-609; 1992
Cho et al. (1993) Science 261:1303

Colbere-Garapin et al., *J. Mol. Biol.* 150, 1-14, 1981
Cole et al., *Mol. Cell Biol.* 62, 109-120, 1984)
Coruzzi et al., *EMBO J.* 3, 1671-1680, 1984
Cote et al., *Proc. Natl. Acad. Sci.* 80,2026-2030; 1983
Couture & Stinchcomb, *Trends Genet.* 12, 510-515, 1996
Cull et al.(1992) Proc. Natl. Acad. Sci. USA 89:1865-1869
Cwirla et al. (1990) Proc. Natl. Acad. Sci. USA 87:6378-6382
Devlin (1990) Science 249:404-406
DeWitt et al. (1993) Proc. Natl. Acad. Sci. USA 90:6909
Engelhard et al., *Proc. Nat. Acad Sci.* 91, 3224-3227, 1994
Erb et al. (1994) Proc. Natl. Acad. Sci. USA 91:11422
Felici (1991) J. Mol. Biol. 222:301-310
Fodor (1993) Nature 364:555-556
Gallop et al. (1994) J. Med. Chem. 37:1233
Gee et al., in Huber & Carr, MOLECULAR AND IMMUNOLOGIC APPROACHES, Futura Publishing Co., Mt. Kisco, N.Y., 1994
Gergen and Weiss, Am Rev Respir Dis 146:823-824, 1992
Gibson, U. E. M., Heid, C. A. and Williams, P. M., Genome Research. 6: 995-1001, 1996.
Hampton et al., SEROLOGICAL METHODS: A LABORATORY MANUAL, APS Press, St. Paul, Minn., 1990
Hartman & Mulligan, *Proc. Natl. Acad. Sci.* 85, 8047-51, 1988
Haseloff et al. *Nature* 334, 585-591, 1988
Heid, C. A., Stevens, J., Livak, K. J., and Williams, P. M., Genome Research, 6: 986-994, 1996.
Holland, P. M., Abramson, R. D., Watson, R. and Gelfand, D. H., PNAS. 88: 7276-7280, 1991.
Hsiang et al., *J. Biol. Chem.* 274, 37161-68, 1999
Horn et al. *Nucl. Acids Res. Symp. Ser.* 225-232, 1980
Houghten (1992) Bio/Techniques 13:412-421
Iwabuchi et al., *Oncogene* 8, 1693-1696, 1993
Jeffreys A J, W. V., Thein S L, Nature. 316: 76-9, 1985.
Johnson et al., *Endoc. Rev.* 10, 317-331, 1989
Kellogg, D. E., et al., Anal. Biochem. 189:202-208 (1990)
Kohler et al., *Nature* 256, 495-497, 1985
Kozbor et al., *J. Immunol. Methods* 81, 31-42, 1985
Konig et al., *Am. J. Physiol. Gastrointest. Liver Physiol.* 278, G156-64, 2000
Kouzuki et al., *J. Pharmacol. Exp. Ther.* 292, 505-11, 2000
Kroll et al., *DNA Cell Biol.* 12, 441-453, 1993
Lam (1991) Nature 354:82-84
Lam (1997) Anticancer Drug Des. 12:145
Lam K S. Application of combinatorial library methods in cancer research and drug discovery.Anticancer Drug Des 1997; April 12(3):145-67
Livak, K. J., Flood, S. J., Marmaro, J., Giusti, W. and Deetz, K., PCR Methods and Applications 357-362, 1995.
Logan & Shenk, *Proc. Natl. Acad Sci.* 81, 3655-3659, 1984
Lowy et al., *Cell* 22, 817-23, 1980
Maddox et al., *J. Exp. Med.* 158,1211-1216, 1983
Madura et al., *J. Biol. Chem.* 268, 12046-12054, 1993
Maniatis et al., Molecular Cloning: A Laboratory Manual, 1982, Cold Spring Harbor Laboratory, Cold Spring Harbor Press
McConnell et al., *Science* 257, 1906-1912, 1992
Merrifield, *J. Am. Chem. Soc.* 85, 2149-2154, 1963
Morrison et al., *Proc. Natl. Acad. Sci.* 81, 6851-6855, 1984
Murray, 1992, supra
Nagarenko, I. A., et al. Nucleic Acids Research 25:16-21 (1997)
Neuberger et al., *Nature* 312, 604-608, 1984
Nicholls et al., 1993, *J. Immunol. Meth.* 165, 81-91)
Piatak, M. J., et al., BioTechniques 14:70-81 (1993)
Piatak, M. J., et al., Science 259:1749-1754 (1993))
Porath et al., *Prot. Exp. Purif.* 3, 263-281, 1992
Roberge et al., *Science* 269, 202-204, 1995
Sambrook, J., Fritsch, E. F., and Maniatis, T. (1989) Molecular Cloning: A Laboratory Manual, 2nd ed., Cold Spring Harbor Laboratory Press, NY.
Scott and Smith (1990) Science 249:386-390
Sharp, P. A., et al., Methods Enzymol. 65:750-768, 1980
Sjolander & Urbaniczy, *Anal. Chem.* 63,2338-2345, 1991
Southern, E. M., J. Mol. Biol., 98:503-517, 1975
Szabo et al., *Curr. Opin. Struct. Biol.* 5, 699-705, 1995
Takamatsu *EMBO J.* 6,307-311, 1987
Takeda et al., *Nature* 314, 452-454, 1985
Thomas, P. S., Proc. Nat. Acad. Sci., 77:5201-5205, 1980)
Uhlmann et al., *Chem. Rev.* 90, 543-584, 1990
Uhlmann et al., *Tetrahedron. Lett.* 215, 3539-3542, 1987
Verhaar et al., 1995, *Int. J. Cancer* 61, 497-501
Weber et al., Genomics. 7: 524-30, 1990.
Wigler et al., *Cell* 11, 223-32, 1977
Wigler et al., *Proc. Natl. Acad. Sci.* 77, 3567-70, 1980
Zervos et al., *Cell* 72, 223-232, 1993
Zuckermann et al. (1994). J. Med. Chem. 37:2678

---

The invention claimed is:

1. An isolated nucleic acid molecule encoding an UST3-LIKE 1 polypeptide comprising the amino acid sequence of SEQ ID NO:2, wherein the polypeptide encoded by said nucleic acid molecule has UST3-LIKE1 activity.

2. A vector comprising the nucleic acid molecule of claim 1.

3. An isolated host cell containing the vector of claim 2.

4. A method of producing a UST3-LIKE 1 polypeptide comprising the steps of
   i) culturing the host cell of claim 2 under suitable conditions and
   ii) recovering the UST3-LIKE 1 polypeptide from the culture medium.

5. The nucleic acid molecule of claim 1 which comprises the sequence of SEQ ID NO: 1.

6. A vector comprising the nucleic acid molecule of claim 5.

7. An isolated host cell containing the vector of claim 6.

8. A method of producing a UST3-LIKE 1 polypeptide comprising the steps of
   i) culturing the host cell of claim 7 under suitable conditions and
   ii) recovering the UST3-LIKE 1 polypeptide from the culture medium.

9. The isolated nucleic acid molecule of claim 5 which consists of the sequence of SEQ ID NO: 1.

10. A vector comprising the nucleic acid molecule of claim 9.

11. An isolated host cell containing the vector of claim 10.

12. A method of producing a UST3-LIKE 1 polypeptide comprising the steps of
    i) culturing the host cell of claim 11 under suitable conditions and
    ii) recovering the UST3-LIKE 1 polypeptide from the culture medium.

* * * * *